(12) United States Patent
Osborne et al.

(10) Patent No.: US 6,723,788 B1
(45) Date of Patent: Apr. 20, 2004

(54) ENZYME INHIBITORS

(75) Inventors: Scott Edward Osborne, Middletown, OH (US); Todd Laurence Underiner, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/658,335

(22) Filed: Sep. 8, 2000

Related U.S. Application Data

(60) Provisional application No. 60/153,418, filed on Sep. 10, 1999.

(51) Int. Cl.$^7$ .................................................. C08F 8/32
(52) U.S. Cl. ................ 525/54.1; 525/328.2; 525/328.8; 525/353; 525/375
(58) Field of Search ............................ 525/54.1, 328.2, 525/328.8, 375, 353

(56) References Cited

U.S. PATENT DOCUMENTS

| | | | |
|---|---|---|---|
| 4,496,689 A | 1/1985 | Mitra ........................ 525/54.1 |
| 5,162,307 A | 11/1992 | Digenis et al. ................ 514/19 |
| 5,571,844 A | 11/1996 | Stüber et al. ................ 514/602 |
| 5,880,131 A | 3/1999 | Greenwald et al. .......... 514/279 |
| 6,113,906 A | 9/2000 | Greenwald et al. ....... 424/194.1 |

FOREIGN PATENT DOCUMENTS

| | | |
|---|---|---|
| EP | 0 452 179 A2 | 10/1991 |
| FR | 2211469 | 7/1974 |
| FR | 2252351 | 6/1975 |
| WO | WO 00/40203 | 7/2000 |

*Primary Examiner*—Bernard Lipman
(74) *Attorney, Agent, or Firm*—Richard S. Echler, Sr.

(57) ABSTRACT

The present invention relates to compositions which comprise one or more polymer conjugates having the formula:

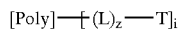

wherein T is a heterocyclic unit which is capable of inhibiting one or more proteolytic enzymes; L is a linking group; [Poly] is a polymeric unit, i indicates the number of said heterocyclic units which comprise said conjugate and has the value of from 1 to 100; z is 0 or 1, said polymer conjugates suitable for use in preventing skin irritation resulting from exposure of the skin to body fluids, inter alia, feces, menstrual fluid. The conjugates of the present invention are useful in diapers, dressings, sanitary napkins, and the like.

41 Claims, No Drawings

ENZYME INHIBITORS

This Application claims priority from U.S. Provisional Application Serial No. 60/153,418 filed Sep. 10, 1999.

FIELD OF THE INVENTION

The present invention relates to novel functional polymer conjugates which inhibit one or more proteolytic and/or lipolytic enzymes. The polymer conjugates described herein are suitable for use in any context wherein proteolytic and/or lipolytic enzyme inhibition is indicated, inter alia, treatment of diaper rash.

BACKGROUND OF THE INVENTION

Diaper rash is ubiquitous. It was once believed that contacting the skin with urine produced diaper rash, however, it is now understood that the irritation of tissue which manifests itself in "diaper rash" is primarily caused by endogenic proteolytic and/or lipolytic enzymes, inter alia, trypsin, chymotrypsin, elastase, pancreatic lipase, which comprise human feces. However, skin irritation is not limited to enzymes which comprise feces, for example, menstrual fluids, nasal fluids, colostomy fluids, dandruff, wound healing may all provide a source of enzymes which produce irritation.

Proteolytic and lipolytic enzyme inhibitors are known. An example of effective inhibitors are "suicide inhibitors" which irreversibly react with the active site of the target enzyme thereby destroying the enzyme's ability to function. Reversible enzyme inhibitors, although not permanently inactivating the target enzyme, are also considered sufficiently effective to inhibit the effects of unwanted enzyme exposure. One drawback of low molecular weight enzyme inhibitors is their propensity to be readily absorbed through skin tissue, thereby entering into human cells wherein normal cell catabolism can be interrupted.

There is a long felt need to provide a barrier against the pernicious enzymes which act to irritate human skin, especially enzymes which produce diaper rash.

SUMMARY OF THE INVENTION

The present invention meets the aforementioned needs in that it has been surprisingly discovered that proteolytic and/or lipolytic enzyme inhibitors can be effectively delivered to human skin wherein said inhibitors can function as a barrier to enzyme activity thereby preventing diaper rash. The enzyme inhibitors of the present invention are polymer conjugates which have an enzyme inhibitor component and a functionalized polymer component.

The enzyme inhibitor component comprises a heterocyclic ring template and an enzyme targeting unit. The functionalized polymer component comprises a moiety which acts as an anchoring template for one or more enzyme inhibitors while providing a means for delivering the conjugate molecule to human skin. The enzyme inhibitor component is optionally, but preferably, linked to the functionalized polymer component by a linking group.

A first aspect of the present invention relates to an enzyme inhibiting polymer conjugate which is capable of inhibiting one or more proteolytic enzymes having the formula:

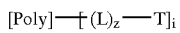

wherein T is a heterocyclic unit; L is a linking group; [Poly] is a polymeric unit, i indicates the number of said heterocyclic units which comprise said conjugate and has the value of from 1 to 100; z is 0 or 1.

The present invention further relates to a process for preventing the formation of skin irritation which is due to the presence of proteolytic and/or lipolytic enzymes, said process comprises the step of contacting an effective amount of a polymer conjugate as described herein below to human skin.

These and other objects, features and advantages will become apparent to those of ordinary skill in the art from a reading of the following detailed description and the appended claims. All percentages, ratios and proportions herein are by weight, unless otherwise specified. All temperatures are in degrees Celsius (°C.) unless otherwise specified. All documents cited are in relevant part, incorporated herein by reference.

DETAILED DESCRIPTION OF THE INVENTION

The present invention relates to the prevention of pernicious and otherwise unwanted skin conditions, inter alia, rash, irritation, which is caused by the contact of proteolytic and/or lipolytic enzymes with skin. Among the conditions which the present invention seeks to ameliorate is diaper rash. The present invention achieves the desired result by applying to the skin by a suitable means a sufficient amount of a polymer conjugate which inhibits the activity of one or more enzymes which are the cause of said unwanted skin condition.

The polymer conjugates of the present invention comprise an enzyme inhibitor component and a functionalized polymer component. The enzyme inhibitor component comprises a heterocyclic ring template and an enzyme targeting unit. Key to the effectiveness of the enzyme inhibitor is the fact that the inhibitor comprises "an enzyme specifying unit" which has been modified.

The enzyme inhibitor component comprises a unit which has the role of either providing specificity for a particular enzyme or assists in deactivating the targeted enzyme.

The conjugates of the present invention further comprise a functionalized polymer component which acts as a delivery template for one or more enzyme inhibitors while providing a means for anchoring the conjugate molecule to human skin. The functionalized polymer component is typically an amphiphilic polymer which is capable of being directly attached to the enzyme inhibitor component or of being attached thereto by a linking unit. The polymer component also provides the conjugate with a source of increased molecular weight which acts to inhibit the absorption of the enzyme inhibitor into skin tissue. The polymer component also acts to facilitate formulation of the enzyme inhibitor into carriers or facilitates deposition of the conjugate directly to skin or by way of a substrate, diaper top sheet, inter alia, to which the conjugate is applied.

The conjugates of the present invention also optionally comprise a linking unit which serves to tether the enzyme inhibitor portion of the conjugate to the polymeric component. Although the polymer may be bonded directly to the enzyme inhibiting heterocycle, preferably a linking group is present to facilitate preparation and attachment of the polymer thereto.

The polymer conjugates of the present invention are utilized in an effective amount. For the purposes of the present invention the term "effective amount" is defined herein as the amount necessary to provide a reduction in enzyme activity in at least one inhibition assay. Preferred assays which are described herein are, inter alia, "Fecal Protease Inhibition Assay", "Skin Test of Inhibition of IL-1α Production". Suitable tests also include tests which differentiate the specificity of said enzyme inhibitor, for example, which differentiate the particular proteases obstructed by said inhibitor.

Polymer Conjugates

Enzyme Inhibitor Component

The enzyme inhibitor component of the present invention comprises one or more heterocyclic moieties, designated herein as T units. The heterocyclic moiety is further characterized in that it comprises a unit (enzyme modulator) which interacts with one or more protease or lipase enzymes. Said heterocyclic moieties further optionally comprise one or more enzyme differentiating units, R.

The heterocyclic moieties of the present invention comprise 2 fused rings; an "A ring" which is common to all of the conjugates and a "B ring" which can vary widely and is further described herein below. The A ring has the formula:

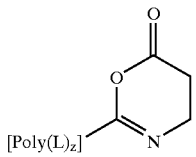

and is the ring which is preferably attached to the optional linking group or directly to the polymer component. It is this ring which is capable of reversibly reacting with a target enzyme via acylation. The acylating unit of the present heterocyclic moieties has a different configuration with respect to prior art acylating units. Key is the fact that the present invention provides for a conjugate which is not linked via the acylating unit itself and secondly the acylating unit is tied back into a ring. This key structural difference prevents the release of the acylating agent upon interaction with an enzyme or a hydrolyzing agent, inter alia, water, urine, body fluids.

The present invention overcomes any pejorative effects from pre-mature hydrolysis of the conjugate. For example, if the enzyme inhibitor component becomes prematurely detached from the polymer component, the inhibitor can then diffuse into healthy skin tissue. This has two immediate effects; the loss of active substrate and the possible infusion of an unwanted active into skin cells. This problem of detachment of the inhibitor component from the polymer component has been overcome by tying back the acylating unit into a ring.

The preferred acylating agent of the present invention is the ester carboxyl unit. A prior art polymer conjugate which is linked to an enzyme inhibitor via the ester carboxyl unit has the formula:

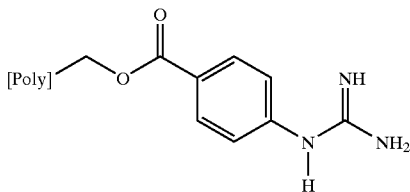

and said conjugate is capable or reacting with a trypsin enzyme active site serine hydroxyl unit to displace the [Poly]-CH$_2$O— unit which corresponds to the present invention as the polymer component. The effect of this reaction is the acylation of the enzyme active site serine hydroxyl moiety. Although specific to attack by the serine hydroxyl unit, this ester linkage is also potentially attacked by other hydrolyzing units. Hydrolysis of the above prior art inhibitor component from the polymer component prior to attack by the desired enzyme has the pejorative effect of potentially prematurely releasing the enzyme inhibitor from the enzyme. Indeed, if the enzyme inhibition takes place in a reversible manner, the inhibitor can be liberated from the enzyme and can diffuse into human skin tissue with potentially deleterious side-effects.

When the 4-guanidinobenzyl unit is incorporated into a polymer conjugate of the present invention, this results in a conjugate having the general formula:

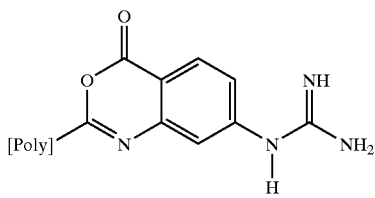

which provides resistance to fragmentation of the inhibitor component from the polymer conjugate while allowing the enzyme inhibitor component to be effectively delivered to enzyme active site via the acyl unit. Without wishing to be limited by theory, once the enzyme has interacted with the conjugate acylating unit, the species which remains will have the proposed formula:

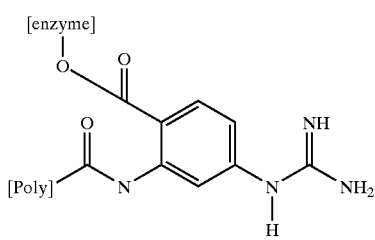

one advantage of which is the polymer component remains linked to the enzyme inhibitor component. If the enzyme interaction is reversible, then the resulting high molecular weight substrate will not be capable of diffusing into human skin tissue. In this manner linking units, especially linking units which are inextricably part of the ring system, can serve to attenuate the interaction of the inhibitor and a target enzyme.

The heterocyclic units of the present invention comprise units having the formula selected from the group consisting of:

i)

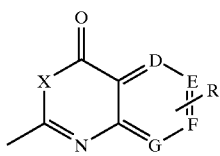

-continued
ii)
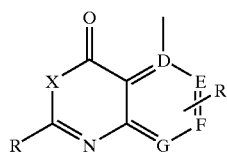
iii)
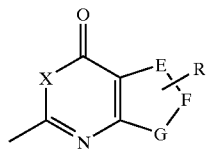
iv)
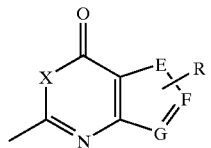
v)
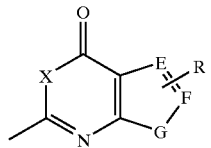
vi)
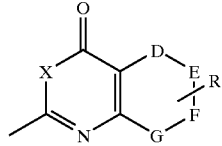
vii)
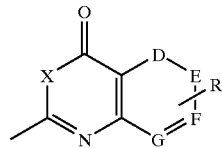
viii)
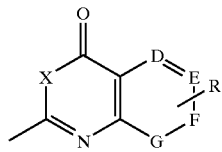
ix)
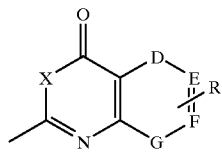
-continued
x)
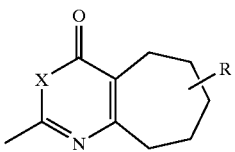
xi) and mixtures thereof;
wherein X is selected from the group consisting of —$CH_2$—, —NH—, —O—, —S—, —$CF_2$—, and mixtures thereof; and each D, E, F, and G is independently selected from the group consisting of —CH—, —$CH_2$—, —N—, —NH—, —O—, —S—, —$CF_2$—, and mixtures thereof.
Preferred heterocyclic units are selected from the group consisting of:
i)
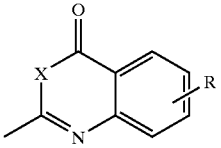
ii)
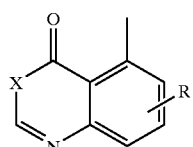
iii)
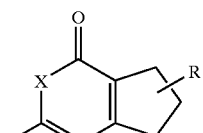
iv)
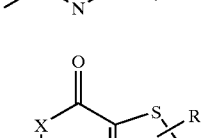
v)
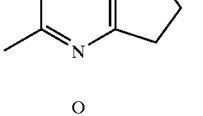
vi)
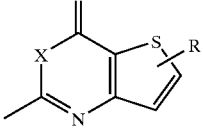

vii) 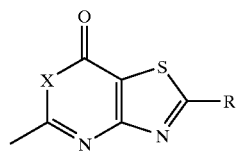
viii) 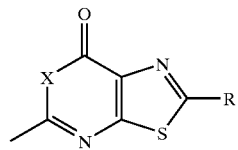
ix) 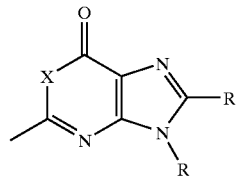
x) 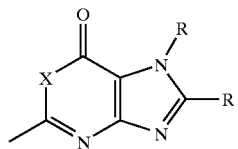
xi) 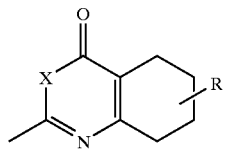
xii) 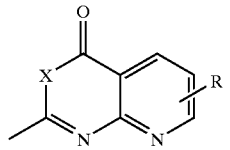
xiii) 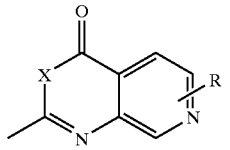
xiv) 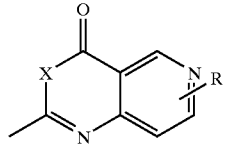
xv) 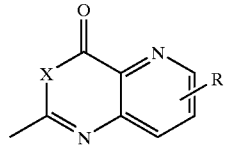
xvi) 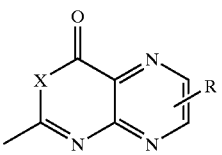
xvii) 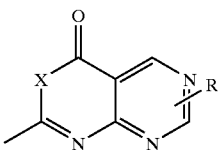
xviii) 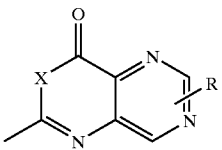
xix) and mixtures thereof.
The preferred heterocycles of the present invention are units having the formula:
i) 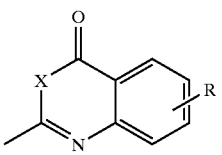
ii) 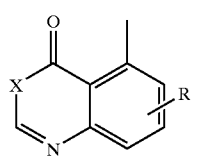
iii) 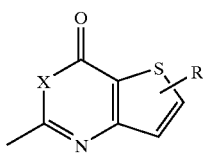
iv) 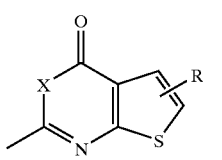
v) 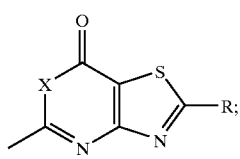

vi)

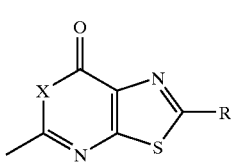

more preferred units have the formula:

i)

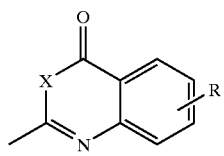

ii)

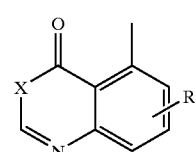

iii)

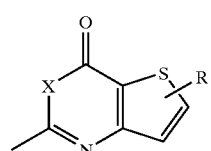

iv)

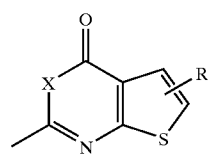

most preferred units are the 4H-3,1-benzoxazin-4-one heterocycles having the formula:

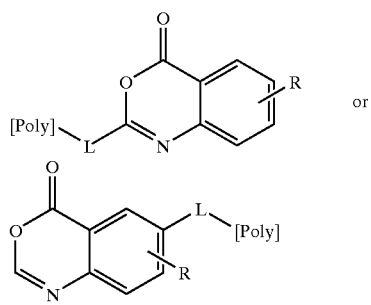 or which are preferably linked to the polymeric component via the 2, 5, or 6 ring position. It will be noted by the formulator that only the exocyclic portion of the linking unit is rendered distinct from the heterocyclic ring system above. The examples herein above can effectively deliver a benzoic acid-like inhibitor, inter alia, 4-guanidinobenzoate, and part of the linking group is taken up as part of the benzoxazin-4-one ring system. Herein below only the exocyclic component of the linking groups are delineated, an the formulator is not restricted in using any part thereof to form other heterocycles which suitably deliver protease and/or lipase inhibitors.

The enzyme inhibition component further comprises one or more enzyme differentiating units, R. R units assist in attenuating the inhibitor/target enzyme interaction by, for example, providing a secondary sight of interaction between the polymer conjugates and the target enzymes. R units are:

a) hydrogen;
b) $C_1$–$C_{18}$ substituted or unsubstituted, linear or branched alkyl; preferably $C_1$–$C_8$ linear unsubstituted alkyl, inter alia, methyl and ethyl, especially when the enzyme inhibitor component comprises a benzoxazin-4-one moiety.
c) $C_3$–$C_{18}$ substituted or unsubstituted, cycloalkyl; preferably $C_6$–$C_{10}$ unsubstituted cycloalkyl;
d) $C_2$–$C_{18}$ substituted or unsubstituted, linear or branched alkenyl; preferably $C_{10}$ and $C_{15}$ branched alkenyl units derived from terpenes or other isoprene derived units;
e) $C_2$–$C_{18}$ substituted or unsubstituted, linear or branched alkynyl;
f) $C_6$–$C_{18}$ substituted or unsubstituted aryl; preferably phenyl, biphenyl, naphthyl and the like;
g) $C_2$–$C_{18}$ substituted or unsubstituted heterocyclic alkyl;
h) $C_3$–$C_{18}$ substituted or unsubstituted heterocyclic alkenyl;
i) alkylenearyl having the formula:

$$-(R^1)_n-R^2$$

wherein $R^1$ is $C_1$–$C_{12}$ linear or branched alkylene, $C_2$–$C_{12}$ linear or branched alkenylene, or mixtures thereof; $R^2$ is $C_6$–$C_{18}$ substituted or unsubstituted aryl, $C_3$–$C_{18}$ heteroaryl, or mixtures thereof; n is from 1 to 16; a preferred alkylenearyl unit comprises substituted benzyl units;

j) an amino unit having the formula:

$$-(CH_2)_m N(R^3)_2$$

wherein each $R^3$ is independently hydrogen, $C_1$–$C_{18}$ substituted or unsubstituted, linear, cyclic, or branched alkyl; m is from 0 to 10;

k) a quaternary ammonium unit having the formula:

$$-(CH_2)_m \overset{+}{N}(R^3)_3 Y^-$$

wherein each $R^3$ is independently hydrogen, $C_1$–$C_{18}$ substituted or unsubstituted, linear, cyclic, or branched alkyl; Y is an anion of sufficient charge to provide electronic neutrality; m is from 0 to 10;

l) a unit having the formula:

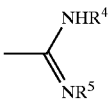

wherein $R^4$ is hydrogen, $C_1$–$C_4$ alkyl, or mixtures thereof; $R^5$ is hydrogen, $C_1$–$C_4$ alkyl, or mixtures thereof; $R^4$ and $R^5$ can be taken together to form a heterocyclic ring comprising from 3 to 5 carbon atoms; preferred is amidine;

m) a unit having the formula:

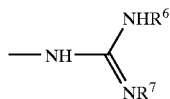

wherein $R^6$ is hydrogen, $C_1$–$C_4$ alkyl, or mixtures thereof; $R^7$ is hydrogen, $C_1$–$C_4$ alkyl, or mixtures thereof; $R^6$ and $R^7$ can be taken together to form a heterocyclic ring comprising from 3 to 5 carbon atoms; preferred are guanidine units and cyclic units, inter alia, imidazolinyl;

n) a unit having the formula:

wherein $R^8$ is:
i) —$(CH_2)_p$—, wherein p is from 0 to 12;
ii) —C(O)—;
iii) —$C(X)NR^{10}$—, wherein $R_{10}$ is hydrogen, $C_1$–$C_4$ alkyl, or mixtures thereof; X is oxygen, sulfur, $NR^{10}$, and mixtures thereof;
iv) —$C(X)R^{11}C(X)$—, wherein $R^{11}$ is $C_1$–$C_{12}$ alkylene, substituted or unsubstituted phenylene, or mixtures thereof; X is oxygen, sulfur, $NR^{10}$, and mixtures thereof;
v) —$C(X)NR^{10}C(X)$—, wherein $R_{10}$ is hydrogen, $C_1$–$C_4$ alkyl, or mixtures thereof; X is oxygen, sulfur, $NR^{10}$, and mixtures thereof;
vi) —$C(X)NR^{10}R^{11}NR^{10}C(X)$—, wherein $R_{10}$ is hydrogen, $C_1$–$C_4$ alkyl, or mixtures thereof; $R^{11}$ is $C_1$–$C_{12}$ alkylene, substituted or unsubstituted phenylene, or mixtures thereof; X is oxygen, sulfur, $NR^{10}$, and mixtures thereof;
vii) —$NR^{10}C(X)$—, wherein $R^{10}$ is hydrogen, $C_1$–$C_4$ alkyl, or mixtures thereof; X is oxygen, sulfur, $NR^{10}$, and mixtures thereof;
viii) —$NR^{10}C(X)NR^{10}$—, wherein $R^{10}$ is hydrogen, $C_1$–$C_4$ alkyl, or mixtures thereof; X is oxygen, sulfur, $NR^{10}$, and mixtures thereof;
ix) —$NR^{10}C(X)R^{11}NR^{10}$—, wherein $R^{10}$ is hydrogen, $C_1$–$C_4$ alkyl, or mixtures thereof; $R^{11}$ is $C_1$–$C_{12}$ alkylene, substituted or unsubstituted phenylene, or mixtures thereof; X is oxygen, sulfur, $NR^{10}$, and mixtures thereof;
x) —$NR^{10}R^{11}C(X)NR^{10}$—, wherein $R^{10}$ is hydrogen, $C_1$–$C_4$ alkyl, or mixtures thereof; $R^{11}$ is $C_1$–$C_{12}$ alkylene, substituted or unsubstituted phenylene, or mixtures thereof; X is oxygen, sulfur, $NR^{10}$, and mixtures thereof;
xi) —$NR^{10}C(X)R^{11}C(X)O$—, wherein $R^{10}$ is hydrogen, $C_1$–$C_4$ alkyl, or mixtures thereof; $R^{11}$ is $C_1$–$C_{12}$ alkylene, substituted or unsubstituted phenylene, or mixtures thereof; X is oxygen, sulfur, $NR^{10}$, and mixtures thereof;
xii) —$OC(X)R^{11}C(X)NR^{10}$—, wherein $R^{10}$ is hydrogen, $C_1$–$C_4$ alkyl, or mixtures thereof; $R^{11}$ is $C_1$–$C_{12}$ alkylene, substituted or unsubstituted phenylene, or mixtures thereof; X is oxygen, sulfur, $NR^{10}$, and mixtures thereof;
xiii) —$NR^{10}C(X)NR^{11}R^{11}$—, wherein $R^{10}$ is hydrogen, $C_1$–$C_4$ alkyl, or mixtures thereof; $R^{11}$ is $C_1$–$C_{12}$ alkylene, substituted or unsubstituted phenylene, or mixtures thereof; X is oxygen, sulfur, $NR^{10}$, and mixtures thereof;
xiv) —$R^{11}NR^{10}C(X)NR^{10}$—, wherein $R^{10}$ is hydrogen, $C_1$–$C_4$ alkyl, or mixtures thereof; $R^{11}$ is $C_1$–$C_{12}$ alkylene, substituted or unsubstituted phenylene, or mixtures thereof; wherein X is oxygen, sulfur, $NR^{10}$, and mixtures thereof;
xv) —$R^{11}NR^{10}C(X)NR^{10}R^{11}$—, wherein $R^{10}$ is hydrogen, $C_1$–$C_4$ alkyl, or mixtures thereof; $R^{11}$ is $C_1$–$C_{12}$ alkylene, substituted or unsubstituted phenylene, or mixtures thereof; X is oxygen, sulfur, $NR^{10}$, and mixtures thereof;
xvi) —$NR^{10}$—, wherein $R^{10}$ is hydrogen, $C_1$–$C_4$ alkyl, or mixtures thereof;
xvii) —O—;
xviii) —$(R^{11})_tC(X)(R^{11})_t$—; wherein $R^{11}$ is $C_1$–$C_{12}$ alkylene, substituted or unsubstituted phenylene, or mixtures thereof; t is 0 or 1; X is oxygen, sulfur, $NR^{10}$, and mixtures thereof;
xix) —$(R^{11})_tOC(O)(R^{11})_t$—; wherein $R^{11}$ is $C_1$–$C_{12}$ alkylene, substituted or unsubstituted phenylene, or mixtures thereof; t is 0 or 1;
xx) —$(R^{11})_tC(O)O(R^{11})_t$—; wherein $R^{11}$ is $C_1$–$C_{12}$ alkylene, substituted or unsubstituted phenylene, or mixtures thereof; t is 0 or 1;
xxi) alkyleneoxyalkylene having the formula:

—$(R^{12}O)_qR^{13}$— wherein $R^{12}$ is $C_2$–$C_6$ linear or branched alkylene, substituted or unsubstituted phenylene; $R^{13}$ is —$(CH_2)_p$—, wherein p is from 0 to 12; q is from 1 to 4;
xxii) —S—;
xxiii) —$(R^{11})_tS(R^{11})_t$—; wherein $R^{11}$ is $C_1$–$C_{12}$ alkylene, substituted or unsubstituted phenylene, or mixtures thereof; t is 0 or 1;
xxiv) —$(R^{11})_tS(O)(R^{11})_t$—; wherein $R^{11}$ is $C_1$–$C_{12}$ alkylene, substituted or unsubstituted phenylene, or mixtures thereof; t is 0 or 1;
xxv) —$(R^{11})_tSO_2(R^{11})_t$—; wherein $R^{11}$ is $C_1$–$C_{12}$ alkylene, substituted or unsubstituted phenylene, or mixtures thereof; t is 0 or 1;
xxvi) or mixtures thereof;
$R^9$ is:
i) hydrogen;
ii) $C_1$–$C_{18}$ substituted or unsubstituted, linear or branched alkyl;
iii) $C_3$–$C_{18}$ substituted or unsubstituted, linear or branched cycloalkyl
iv) $C_2$–$C_{18}$ substituted or unsubstituted, linear or branched alkenyl;
v) $C_2$–$C_{18}$ substituted or unsubstituted, linear or branched alkynyl;
vi) $C_6$–$C_{18}$ substituted or unsubstituted aryl;
vii) $C_2$–$C_{18}$ substituted or unsubstituted heterocyclic alkyl;
viii) $C_3$–$C_{18}$ substituted or unsubstituted heterocyclic alkenyl;
ix) —OH;
x) —$SO_3M$, wherein M is hydrogen or a water soluble cation;
xi) —$OSO_3M$, wherein M is hydrogen or a water soluble cation;
xii) —$NO_2$;
xiii) halogen selected from fluorine, chlorine, bromine, iodine, or mixtures thereof;
xiv) —$C(Hal)_3$, wherein each Hal is fluorine, chlorine, bromine, iodine, or mixtures thereof;
xv) —$COR^{14}$; wherein $R^{14}$ is hydrogen, —OH, $C_1$–$C_{12}$ alkyl, $C_1$–$C_{12}$ alkoxy, or mixtures thereof; —$N(R^{15})_2$, or mixtures thereof; each $R^{15}$ is independently hydrogen, —OH, $C_1$–$C_4$ alkyl, or mixtures thereof;

xvi) —CH(OR$^{14}$)$_2$ wherein R$^4$ is hydrogen, $C_1$–$C_{12}$ alkyl, or two R$^{14}$ units can be taken together to form a ring having from 3 to 5 carbon atoms; or mixtures thereof;

xvii) a unit having the formula:

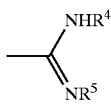

wherein R$^4$ is hydrogen, $C_1$–$C_4$ alkyl, or mixtures thereof; R$^5$ is hydrogen, $C_1$–$C_4$ alkyl, or mixtures thereof; R$^4$ and R$^5$ can be taken together to form a heterocyclic ring comprising from 3 to 5 carbon atoms;

xviii) a unit having the formula:

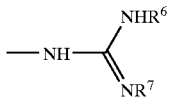

wherein R$^6$ is hydrogen, $C_1$–$C_4$ alkyl, or mixtures thereof; R$^7$ is hydrogen, $C_1$–$C_4$ alkyl, or mixtures thereof; R$^6$ and R$^7$ can be taken together to form a heterocyclic ring comprising from 3 to 5 carbon atoms;

xix) —NHOR$^{16}$, wherein R$^{16}$ is hydrogen; $C_1$–$C_{12}$ linear or branched alkyl; acyl having the formula —COR$^{17}$, wherein R$^{17}$ is $C_1$–$C_4$ alkyl; or mixtures thereof;

xx) a unit having the formula:

—CH=NOR$^{16}$ wherein R$^{16}$ is hydrogen; $C_1$–$C_{12}$ linear or branched alkyl; $C_7$–$C_{22}$ linear or branched alkylenearyl; acyl having the formula —COR$^{17}$, R$^{17}$ is $C_1$–$C_4$ alkyl; or mixtures thereof;

xxi) an amino unit having the formula:

—(CH$_2$)$_m$N(R$^3$)$_2$ wherein each R$^3$ is independently $C_1$–$C_{18}$ substituted or unsubstituted, linear or branched alkyl; m is from 0 to 10;

xxii) a quaternary ammonium unit having the formula:

—(CH$_2$)$_m\overset{+}{N}$(R$^3$)$_3$Y$^-$ wherein each R$^3$ is independently $C_1$–$C_{18}$ substituted or unsubstituted, linear or branched alkyl; Y is an anion of sufficient charge to provide electronic neutrality; m is from 0 to 10;

o) two R units on the same carbon atom can be taken together to form a carbonyl unit or carbonyl unit equivalent, inter alia, C=O, C=NH; and p) mixtures thereof.

Preferred R units according to the present invention include:

a) hydrogen;

b) $C_1$–$C_8$ linear unsubstituted alkyl, for example, methyl, ethyl, propyl, isopropyl, n-butyl, t-butyl, n-pentyl, isopentyl, n-hexyl, 2-methyl hexyl, 2-ethyl, hexyl, Methyl and ethyl are especially preferred when the enzyme inhibitor component comprises a benzoxazin-4-one moiety.

c) $C_6$–$C_{10}$ unsubstituted cycloalkyl, for example cyclohexyl, 4-methylcyclohexyl, 4-isopropylcyclohexyl;

d) $C_{10}$ and $C_{15}$ branched alkenyl units derived from terpenes or other isoprene derived units, for example, 3,7-dimethyl-6-octen-1-yl; 3,7-dimethyl-2,6-octadien-1-yl; 3,7-dimethyl-1,6-octadien-3-yl;

f) phenyl, naphthyl, 4-methoxyphenyl, 4-nitrophenyl, 4-($C_1$–$C_4$ alkyl)phenyl;

g) $C_4$–$C_6$ substituted or unsubstituted heterocyclic alkyl; non-limiting examples of which include 2-furyl, 3-furyl, 2-thienyl, 3-thienyl, 2-pyrrolindinyl, 3-pyrrolidinyl, 2-piperazinyl, N-piperidinyl, 2-piperidinyl, 3-piperidinyl, 4-piperidinyl, N-morpholinyl, and mixtures thereof;

h) $C_3$–$C_{18}$ substituted or unsubstituted heterocyclic alkenyl; 2-pyrrolyl, 3-pyrrolyl;

i) alkylenearyl having the formula:

—CH$_2$—R$^2$ wherein R$^2$ phenyl, substituted phenyl, pyridinyl, substituted pyridinyl;

j) an amino unit having the formula:

—N(R$^3$)$_2$ wherein each R$^3$ is independently hydrogen, methyl, ethyl, 2-hydroxyethyl, cyclopropyl; for example, methylamino, dimethylamino, ethylamino, diethylamino, dicyclopropyl;

l) a unit having the formula:

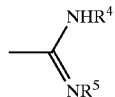

wherein R$^4$ and R$^5$ are each hydrogen, R$^4$ and R$^5$ is taken together to form a heterocyclic ring comprising from 3 to 5 carbon atoms; preferably amidine, 2-pyridinyl, pyrimidinyl, imidazolyl;

m) a unit having the formula:

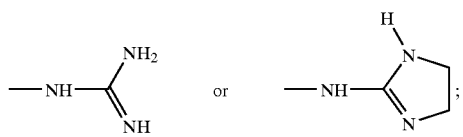

n) a unit having the formula:

—R$^8$—R$^9$ wherein R$^8$ is:

i) —(CH$_2$)$_p$—, wherein p is from 0 to 12;

ii) —C(O)—;

xvi) —NR$^{10}$—, wherein R$^{10}$ is hydrogen, $C_1$–$C_4$ alkyl, or mixtures thereof;

xvii) —O—;

xxi) alkyleneoxyalkylene having the formula:

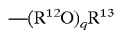

wherein $R^{12}$ is $C_2$–$C_6$ linear or branched alkylene, substituted or unsubstituted phenylene; $R^{13}$ is —$(CH_2)_p$—, wherein p is from 0 to 12; q is from 1 to 4;

xxii) —S—;

xxvi) or mixtures thereof;

$R^9$ is:

i) methyl, ethyl, propyl, isopropyl, n-butyl, isobutyl; preferably methyl when $R^8$ is —O—;

ii) cyclopentyl, cyclohexyl, 4-methylcyclohexyl, 2,5-dimethylcyclopentyl;

v) phenyl, 4-methoxyphenyl, 4-nitrophenyl, 3-chlorophenyl, 4-chlorophenyl, 3,5-dichlorophenyl, 4-aminobenzyl, 4-guanidiobenzyl;

vi) N-aziridinyl, 2-pyrrolindinyl, 3-pyrrolidinyl, 2-piperidinyl, 3-piperidinyl, 4-piperidinyl;

viii) —OH, when the index p is from 1 to 4, preferably when p is 1;

ix) —$SO_3M$ when the index p is from 1 to 4, preferably when p is 1;

x) —$OSO_3M$ when the index p is from 2 to 4, preferably when p is 2;

xi) —$NO_2$;

xii) chlorine, bromine, or mixtures thereof; more preferably chlorine;

xiii) —$CF_3$;

xiv) —$CO_2R^{14}$; wherein $R^{14}$ is hydrogen, —$NH_2$, —$N(CH_3)_2$, or mixtures thereof;

xvii) —$NHOR^{16}$, wherein $R^{16}$ is hydrogen; $C_1$–$C_{12}$ linear or branched alkyl; acyl having the formula —$COR^{17}$, wherein $R^{17}$ is $C_1$–$C_4$ alkyl; or mixtures thereof;

xviii) a unit having the formula:

—CH=$NOR^{16}$ wherein $R^{16}$ is hydrogen, or methyl; and p) mixtures thereof.

For the purposes of the present invention the term "substituted or unsubstituted, linear or branched" is defined herein as the following. Alkyl chains which comprise, for example, a $C_1$–$C_{18}$ alkyl unit will have any combination of carbon atoms arranged in linear form or with one or more branching chains provided the total number of carbons is from 1 to 18 carbon atoms. By the term "substituted" is meant any unit which suitably replaces a hydrogen atom of a linear or branched chain, non-limiting examples of which include halogen, hydroxyl, nitro, amino, cyano, —$CO_2M$, —$SO_3M$, —$OSO_3M$, wherein M is a water soluble cation. For alkenyl units, one or more double bonds may be present and said bonds may be conjugated or non-conjugated. Alkenyl units also include allenes. For aryl units, substituents may comprise alkyl units as well as halogen, etc.

R units can take any form which modulates the enzyme inhibition properties of the T unit. For example, R units under (i) above are alkylenearyl having the formula:

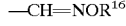

wherein $R^1$ is $C_1$–$C_{12}$ linear or branched alkylene, $C_2$–$C_{12}$ linear or branched alkenylene, or mixtures thereof; $R^2$ $C_6$–$C_{18}$ substituted or unsubstituted aryl, $C_3$–$C_{18}$ heteroaryl, or mixtures thereof; n is from 1 to 16. Non-limiting examples of suitable heteroaryl units are 5-member rings which have the formula:

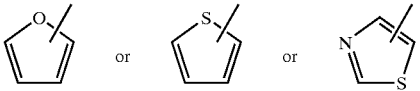

or a 6-member ring having the formula:

wherein said unit can be attached at any carbon atom.

Non-limiting examples of heterocyclic units suitable for use in the present invention include thienyl, furyl, pyrrolyl, pyridinyl, pyrazinyl, thiazolyl, pyrimidinyl, quinolinyl, triazolyl, tetrazolyl, benzothiazolyl, benzofuryl, indolyl, indenyl, azulenyl, fluorenyl, oxazolyl, isoxazolyl, isotriazolyl, imidazolyl, pyraxolyl, oxadiazolyl, indolizinyl, indolyl, isoindolyl, purinyl, quinolizinyl, quinolinyl, isoquinolinyl, cinnolinyl, and mixtures. The heterocyclic ring can be substituted, for example, 2-pyridinecarboxylic acid (picolinyl). The heterocyclic ring can be incorporated in any manner, for example, as a 2-pyridinyl unit (picolyl) or bonded to the heteroatom, for example, N-aziridinyl, N-pyrrolidinyl.

Conjugates of the present invention which are salts or salt-forming compounds will preferably have counter ions which facilitate delivery or formulation. For example, preferred cations include sodium, potassium, lithium, ammonium, alkylammonium, and the like. Preferred anions include halogen, preferably chlorine, methylsulfate, and the like. However, di-basic acids, inter alia, oxalic, fumaric, succinic, may be used to form deliverable salts as well.

Polymeric Component

The polymeric component of the present invention comprises units which provide the herein described conjugates with one or more properties which facilitate the delivery of the enzyme inhibitor to the required substrate.

The polymeric unit or the present invention, represented by [Poly]- can be bonded directly to the enzyme inhibiting component or can be attached by way of a linking unit.

The polymeric materials of the present invention comprise:

i) a polyalkyleneoxy unit having the formula:

wherein $R^{18}$ is $C_2$–$C_{12}$ linear alkylene, $C_3$–$C_{12}$ branched alkylene, phenylene, $C_7$–$C_{12}$ alkylenearylene, and mixtures thereof; $R^{19}$ is hydrogen, $C_1$–$C_{18}$ substituted or unsubstituted, linear or branched alkyl; $C_3$–$C_{18}$ substituted or unsubstituted, linear or branched cycloalkyl; $C_2$–$C_{18}$ substituted or unsubstituted, linear or branched alkenyl; $C_2$–$C_{18}$ substituted or unsubstituted, linear or branched alkynyl; $C_6$–$C_{18}$ substituted or unsubstituted aryl; and mixtures thereof. The index x has the value of from about 10 to about 500. The polyalkyleneoxy unit may be a homopolymer, (e.g., all ethyleneoxy units), co-polymer (e.g., a mixture of ethyleneoxy and propyleneoxy units), or a block co-polymer. The average molecular weight of a polyalkyleneoxy polymeric unit according to the present invention is from about 400 daltons, preferably from about 1500 daltons, more preferably from about 3400 daltons to about 35,000 daltons, preferably to about 20,000 daltons, more preferably to about 10,000 daltons, most preferably to about 8000 daltons.

ii) a co-polymeric polyalkyleneoxy unit having the formula:

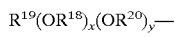

wherein $R^{18}$ is $C_2$–$C_{12}$ linear alkylene, $C_3$–$C_{12}$ branched alkylene, phenylene, $C_7$–$C_{12}$ alkylenearylene, and mixtures thereof; $R^{19}$ is hydrogen, $C_1$–$C_{18}$ substituted or unsubstituted, linear or branched alkyl; $C_3$–$C_{18}$ substituted or unsubstituted, linear or branched cycloalkyl; $C_2$–$C_{18}$ substituted or unsubstituted, linear or branched alkenyl; $C_2$–$C_{18}$ substituted or unsubstituted, linear or branched alkynyl; $C_6$–$C_{18}$ substituted or unsubstituted aryl; and mixtures thereof; $R^{20}$ is a unit selected from:
a) a unit having the formula:

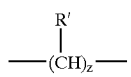

wherein R' is hydrogen, methyl, allyl, hydroxyl, a linking group L which links an enzyme inhibiting component to the polymeric component as described herein below; —(CH$_2$)$_z$—J wherein J is selected from the group consisting of hydrogen, —CO$_2$M, —OSO$_3$M, —SO$_3$M, —OPO$_3$M, —PO$_3$M, —N(R")$_2$, —C(O)N(R")$_2$, —NHC(=NH)NH$_2$, —CCl$_3$, —CF$_3$, and mixtures thereof, wherein R" is hydrogen, $C_1$–$C_4$ alkyl, or mixtures thereof; M is a water soluble cation, preferably ammonium, sodium, or potassium; z is from 1 to 12, z' is from 0 to 6; z +z' is preferably less than 7. The index x has the value of from about 10 to about 500. The index y has the value of from about 10 to about 100.
b) a unit having the formula:

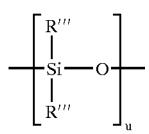

wherein R''' is $C_1$–$C_4$ alkyl, $C_1$–$C_4$ alkoxy, phenyl, a continuation of the chain by branching, or mixtures or mixtures; u has the value of from about 3 to 100. The molecular weight of a polymeric component which comprises a co-polymeric polyalkyleneoxy unit is such that the desired viscosity and solubility of the entire molecule fits the needs of the formulator. For example, units from (a) which comprise one or more linking units to enzyme inhibiting components may incorporate one or more hydrophilic units into the chain to increase the solubility of the final conjugate polymer. However, any of the polymers described herein can be random co-polymers or block co-polymers.

iii) a polysaccharide unit having the formula:

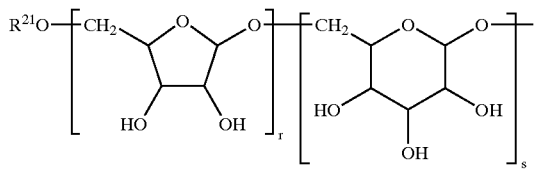

wherein $R^{21}$ is hydrogen, $C_1$–$C_4$ alkyl, and mixtures thereof; the indices r and s are each independently from 0 to 100. The polysaccharide units of the present invention can be any mixture of 5 and 6-member ring sugar units, inter alia, sucrose, glucose, mannose, fructose.

iii) a polyamine unit having the formula:

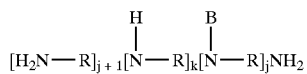

R is $C_2$–$C_{12}$ linear alkylene, $C_3$–$C_{12}$ branched alkylene, and mixtures thereof; preferably R is ethylene, 1,3-propylene, and 1,6-hexylene, more preferred is ethylene. The indices j and k are such that the molecular weight of said polyamines does not exceed about 30,000 daltons. For example, for an entirely linear polyethyleneimine having a molecular weight of about 600 daltons, the index k is equal to 13 and j is equal to 0. For an entirely branched polyethyleneimine having a molecular weight of approximately 600 daltons, the index j is equal to 7. (This combination of indices results in a material having an average molecular weight of about 646 daltons, which, for the purposes of the present invention is a low molecular weight polyalkyleneimine.) The enzyme inhibiting component may be linked or directly bonded to any of the backbone nitrogen units.

The polymeric component of the present invention may be a mixture of one or more of the polymeric units described herein above. In addition, the formulator may attach to the polymeric component of the polymer conjugate as many linking units as necessary to deliver the required number of enzyme inhibiting components. One preferred permutation of admixtures of different components are star polymers as described in "Synthesis of Star-Shaped Poly(ethylene oxide)", Y. Gnanou, et al., *Makromolecular Chemistry*, Vol. 189 (1988) pp. 2885–2892, U.S. Pat. No. 5,648,506 Desai et al., issued Jul. 15, 1997, each of which is incorporated herein by reference.

The preferred polymer or copolymer unit [Poly] of the present invention are polyalkyleneoxy unit having the formula:

and co-polymeric polyalkyleneoxy units having the formula:

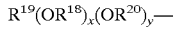

wherein $R^{19}$ is preferably methyl for conjugates which comprise one enzyme inhibitor component, $R^{19}$ is preferably hydroxyethyl for conjugates comprising two enzyme inhibitor components. For the latter, the preferred [Poly] units have the formulae:

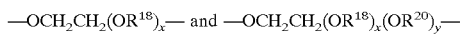

$R^{18}$ is preferably ethylene and $R^{20}$ is preferably 2-propylene and when $R^{18}$, $OR^{19}$, and $OR^{20}$ are taken together the [Poly] unit has a molecular weight of from about 500 daltons, preferably from about 1000 daltons, more preferably from about 2000 daltons, most preferably from about 3000 daltons to about 10,000 daltons, preferably to about 8,000 daltons, more preferably to about 7500 daltons. Preferred

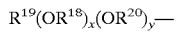

units are copolymer having random polymer units, for example, using EO for ethyleneoxy and PO for propyleneoxy, units having a formula:

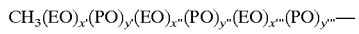

wherein x'+x"+x'"+y'+y"+y'" represent a copolymer having a molecular weight of from about 500 daltons, preferably from about 1000 daltons, more preferably from about 2000 daltons, most preferably from about 3000 daltons to about 10,000 daltons, preferably to about 8,000 daltons, more preferably to about 7500 daltons.

Non-limiting examples of suitable polyalkyleneoxy polymers for use in the present invention include polyethyleneglycol having an average molecular weight of 1500 daltons (PEG 1500), 4000 daltons (PEG 4000), polyethyleneglycol having an average molecular weight of 5000 daltons (PEG 5000), polyethyleneglycol methyl ether having an average molecular weight of 1500 daltons (MPEG 1500), polyethyleneglycol methyl ether having an average molecular weight of 4000 daltons (MPEG 4000), polyethyleneglycol methyl ether having an average molecular weigh of 5000 daltons (MPEG 5000), block co-polymers of polyethylene glycol and polypropylene glycol (EO/PO co-polymers, wherein said PO unit can be 1,2-propylene, 1,3-propylene, or mixtures thereof), and EO/PO/EO and PO/EO/PO co-polymers, for example Pluronics® available ex BASF. One important embodiment of the present invention relates to conjugates which comprise multiple enzyme inhibitor components. This can be done by the formulator to increase the relative amount of inhibitor on a per weight basis of conjugate or to deliver multiple inhibitors per conjugate. The following are non-limiting examples of polyhydroxy units which are suitable for this embodiment.

a)

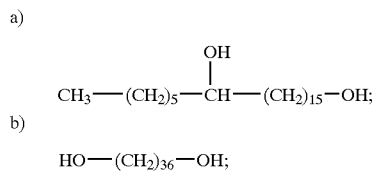

b)

c)

d)

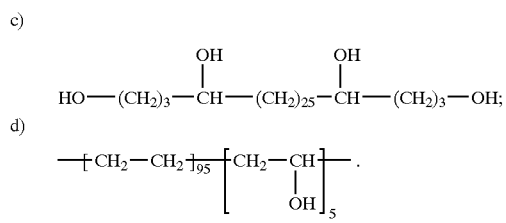

Linking Units

The enzyme inhibiting polymer conjugates of the present invention optionally, but preferably, comprise one or more linking units, L. When the polymer component is bonded to more than one enzyme inhibiting units, the conjugate may comprise more than one linking unit. In addition, more than one type of linking unit may be present. For example, one type of linking unit may be convenient for one particular inhibitor component whereas a second unit is more compatible with a second type of heterocyclic enzyme inhibiting unit.

The linking units of the present invention may comprise any units capable of linking the enzyme inhibitor component to the polymer backbone. If the backbone is formed by random co-polymerization, the linking unit may be included. The linking group may be attached via "grafting" to the polymer backbone. Units which may conveniently serve as linking units are amino acids which have a carboxyl end and an amine end and which are capable of easy assembly into polymeric units (peptides). One or more amino acids taken together are a preferred means for linking the polymer unit and the enzyme inhibitor unit.

Preferred linking units of the present invention have the formula:

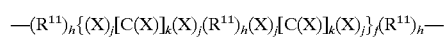

wherein the unit having the formula:

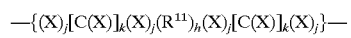

is preferably a repeatable unit, inter alia, amino acid, di-acid, wherein $R^{11}$ is $C_1$–$C_{12}$ substituted or unsubstituted alkylene; $C_2$–$C_{12}$ substituted or unsubstituted alkenylene; $C_3$–$C_{12}$ cycloalkylene; substituted or unsubstituted aromatic; inter alia, 1,2-phenylene, 5-sulfo-1,3-phenylene, 1,4-phenylene; substituted or unsubstituted heterocyclic, non-limiting examples of which include benzimidazole, benzimidazolone, pyridine, piperazine, pyrroline, imidazoline, imidazole, morpholine, oxazole, tetrazole, 1H-indenedione, oxazoline, quinoline, isoquinoline, thiazine, thiazole, benzothiophene, all of which can be linked either through a carbon atom or a heteroatom. The $R^{11}$ units can be substituted or unsubstituted with any of the herein above defined —$R^8R^9$ units. X is oxygen, sulfur, $NR^{10}$ wherein $R^{10}$ is hydrogen, $C_1$–$C_4$ alkyl, phenyl, or $R^{10}$ can be taken as part of a ring bonded to another moiety in the linking group, for example, a propylene unit forming a ring between the nitrogen and $R^{11}$ as in the formula:

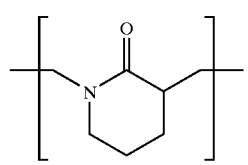

The indices h, j, and k are each independently 0 or 1. As indicated herein above amino acids are a suitable and a preferred class of linking units, either alone, in combination with other amino acids, or other $R^{11}$ units. The index f has the value from 0 to 10. An example of a linking unit comprising a repeatable unit (amino acid) wherein the index f greater than 1 is a linking unit having the general formula:

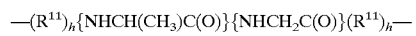

wherein a first repeatable unit is an alanine residue and a second repeatable u nit is a glycine residue. However, depending upon the value of the index f, any combination of repeatable units can be taken together to form a linking unit, for example, a linking unit having the formula:

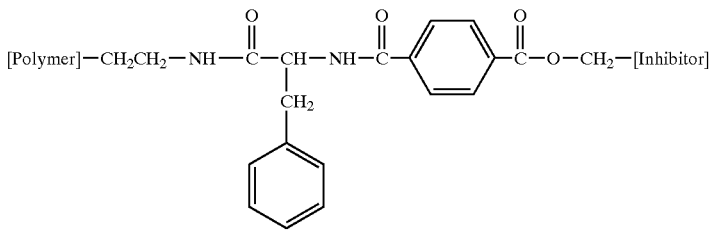

The preferred linking units of the present invention comprise one or more units selected from the group consisting of:
i) —(CH$_2$)$_p$—, wherein p is from 0 to 12;
ii) —C(O)—;
iii) —C(X)NR$^{10}$—, wherein R$^{10}$ is hydrogen, C$_1$–C$_4$ alkyl, or mixtures thereof; X is oxygen, sulfur, NR$^{10}$, and mixtures thereof;
iv) —C(X)R$^{11}$C(X)—, wherein R$^{11}$ is C$_1$–C$_{12}$ alkylene, substituted or unsubstituted phenylene, or mixtures thereof; X is oxygen, sulfur, NR$^{10}$, and mixtures thereof;
v) —C(X)NR$^{10}$C(X)—, wherein R$^{10}$ is hydrogen, C$_1$–C$_4$ alkyl, or mixtures thereof; X is oxygen, sulfur, NR$^{10}$, and mixtures thereof;
vi) —C(X)NR$^{10}$R$^{11}$NR$^{10}$C(X)—, wherein R$^{10}$ is hydrogen, C$_1$–C$_4$ alkyl, or mixtures thereof; R$^{11}$ is C$_1$–C$_{12}$ alkylene, substituted or unsubstituted phenylene, or mixtures thereof; X is oxygen, sulfur, NR$^{10}$, and mixtures thereof;
vii) —NR$^{10}$C(X)—, wherein R$^{10}$ is hydrogen, C$_1$–C$_4$ alkyl, or mixtures thereof; X is oxygen, sulfur, NR$^{10}$, and mixtures thereof;
viii) —NR$^{10}$C(X)NR$^{10}$—, wherein R$^{10}$ is hydrogen, C$_1$–C$_4$ alkyl, or mixtures thereof; X is oxygen, sulfur, NR$^{10}$, and mixtures thereof;
ix) —NR$^{10}$C(X)R$^{11}$NR$^{10}$—, wherein R$^{10}$ is hydrogen, C$_1$–C$_4$ alkyl, or mixtures thereof; R$^{11}$ is C$_1$–C$_{12}$ alkylene, substituted or unsubstituted phenylene, or mixtures thereof; X is oxygen, sulfur, NR$^{10}$, and mixtures thereof;
x) —NR$^{10}$R$^{11}$C(X)NR$^{10}$—, wherein R$^{10}$ is hydrogen, C$_1$–C$_4$ alkyl, or mixtures thereof; R$^{11}$ is C$_1$–C$_{12}$ alkylene, substituted or unsubstituted phenylene, or mixtures thereof; X is oxygen, sulfur, NR$^{10}$, and mixtures thereof;
xi) —NR$^{10}$C(X)R$^{11}$C(X)O—, wherein R$^{10}$ is hydrogen, C$_1$–C$_4$ alkyl, or mixtures thereof; R$^{11}$ is C$_1$–C$_{12}$ alkylene, substituted or unsubstituted phenylene, or mixtures thereof; X is oxygen, sulfur, NR$^{10}$, and mixtures thereof;
xii) —OC(X)R$^{11}$C(X)NR$^{10}$—, wherein R$^{10}$ is hydrogen, C$_1$–C$_4$ alkyl, or mixtures thereof; R$^{11}$ is C$_1$–C$_{12}$ alkylene, substituted or unsubstituted phenylene, or mixtures thereof; X is oxygen, sulfur, NR$^{10}$, and mixtures thereof;
xiii) —NR$^{10}$C(X)NR$^{10}$R$^{11}$—, wherein R$^{10}$ is hydrogen, C$_1$–C$_4$ alkyl, or mixtures thereof; R$^{11}$ is C$_1$–C$_{12}$ alkylene, substituted or unsubstituted phenylene, or mixtures thereof; X is oxygen, sulfur, NR$^{10}$, and mixtures thereof;
xiv) —R$^{11}$NR$^{10}$C(X)NR$^{10}$—, wherein R$^{10}$ is hydrogen, C$_1$–C$_4$ alkyl, or mixtures thereof; R$^{11}$ is C$_1$–C$_{12}$ alkylene, substituted or unsubstituted phenylene, or mixtures thereof; X is oxygen, sulfur, NR$^{10}$, and mixtures thereof;
xv) —R$^{11}$NR$^{10}$C(X)NR$^{10}$R$^{11}$—, wherein R$^{10}$ is hydrogen, C$_1$–C$_4$ alkyl, or mixtures thereof; R$^{11}$ is C$_1$–C$_{12}$ alkylene, substituted or unsubstituted phenylene, or mixtures thereof; X is oxygen, sulfur, NR$^{10}$, and mixtures thereof;
xvii) —O—;
xviii) —(R$^{11}$)$_t$C(X)(R$^{11}$)$_t$—; wherein R$^{11}$ is C$_1$–C$_{12}$ alkylene, substituted or unsubstituted phenylene, or mixtures thereof; t is 0 or 1; wherein X is oxygen, sulfur, NR$^{10}$, and mixtures thereof;
xix) —(R$^{11}$)$_t$OC(O)(R$^{11}$)$_t$—; wherein R$^{11}$ is C$_1$–C$_{12}$ alkylene, substituted or unsubstituted phenylene, or mixtures thereof; t is 0 or 1;
xx) —(R$^{11}$)$_t$C(O)O(R$^{11}$)$_t$—; wherein R$^{11}$ is C$_1$–C$_{12}$ alkylene, substituted or unsubstituted phenylene, or mixtures thereof; t is 0 or 1;
xxi) —(R$^{11}$)$_t$OC(O)O(R$^{11}$)$_t$—; wherein t is 0 or 1;
xxii) alkyleneoxyalkylene having the formula:

—(R$^{12}$O)$_q$R$^{13}$— wherein R$^{12}$ is C$_2$–C$_6$ linear or branched alkylene, substituted or unsubstituted phenylene; R$^{13}$ is —(CH$_2$)$_p$—, wherein p is from 0 to 12; q is 1 or 2;
xxiii) —S—;
xxiv) —(R$^{11}$)$_t$S(R$^{11}$)$_t$—; wherein R$^{11}$ is C$_1$–C$_{12}$ alkylene, substituted or unsubstituted phenylene, or mixtures thereof; t is 0 or 1;
xxv) —(R$^{11}$)$_t$S(O)(R$^{11}$)$_t$—; wherein R$^{11}$ is C$_1$–C$_{12}$ alkylene, substituted or unsubstituted phenylene, or mixtures thereof; t is 0 or 1;
xxvi) —(R$^{11}$)$_t$SO$_2$(R$^{11}$)$_t$—; wherein R$^{11}$ is C$_1$–C$_{12}$ alkylene, substituted or unsubstituted phenylene, or mixtures thereof; t is 0 or 1;
xxvii) or mixtures thereof.

More preferred L units according to the present invention include:
i) —C(O)—;
ii) —C(O)NH—;
iii) —C(O)R$^{11}$C(O)—, wherein R$^{11}$ is methylene, ethylene, propylene, butylene, or mixtures thereof;
iv) —C(O)NHC(O)—;
v) —C(O)NHR$^{11}$NHC(O)— wherein R$^{11}$ is methylene, ethylene, propylene, butylene, or mixtures thereof;
vi) —NHC(O)—;
vii) —NHC(O)NH—;
viii) —C(O)R$^{11}$NH—, R$^{11}$ is C$_1$–C$_{12}$ alkylene, substituted or unsubstituted phenylene, or mixtures thereof;
ix) —NHR$^{11}$C(O)—, R$^{11}$ is C$_1$–C$_{12}$ alkylene, substituted or unsubstituted phenylene, or mixtures thereof;

x) —NH—;
xi) —O—;
xii) —R$^{11}$OC(O)R$^{11}$—; wherein R$^{11}$ is methylene, ethylene, propylene, butylene, or mixtures thereof;
xiii) —R$^{11}$C(O)OR$^{11}$—; wherein R$^{11}$ is methylene, ethylene, propylene, butylenes, or mixtures thereof;
xiv) or mixtures thereof.

The following are non-limiting examples of polymer conjugates according to the present invention.

Preferred polymer conjugates according to the present invention are the mono-inhibitors having the general formula:

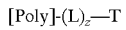
[Poly]-(L)$_z$—T and the bis-inhibitors having the general formula:

T—(L)$_z$-[Poly]-(L)$_z$—T.

Non-limiting examples of preferred mono-inhibitors include:

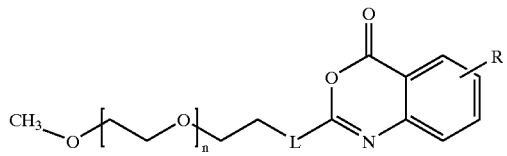

wherein L is O, NH, or mixtures thereof; and the index n has the value such that the polymer component derives from MPEG's having an average molecular weight of 2000 daltons, 5000 daltons, 7000 daltons and mixtures thereof.

Non-limiting examples of preferred bis-inhibitors include:

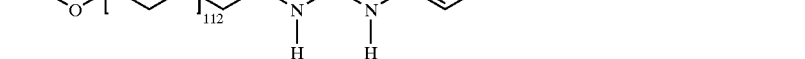

wherein L is O or NH, and the index n has the value such that the polymer component derives from PEG's having an average molecular weight of 1500 daltons, 3400 daltons, 8000 daltons and mixtures thereof.

A preferred polymer conjugate comprises a 4H-benzoxazin-4-one heterocyclic unit wherein each R unit is hydrogen which is linked by an ethyleneimine unit to a polyethyleneglycol polymer component having an average molecular weight of about 5000 daltons having the formula:

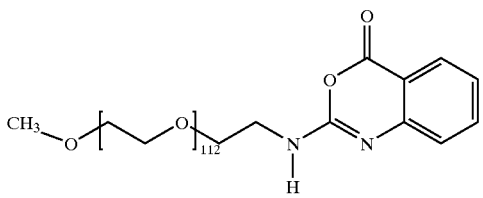

Another preferred polymer conjugate comprises a 4H-benzoxazin-4-one heterocyclic unit wherein each R unit is hydrogen which is linked by an N-ethylene-N'-phenylene urea unit to a polyethyleneglycol polymer component having an average molecular weight of about 5000 daltons having the formula:

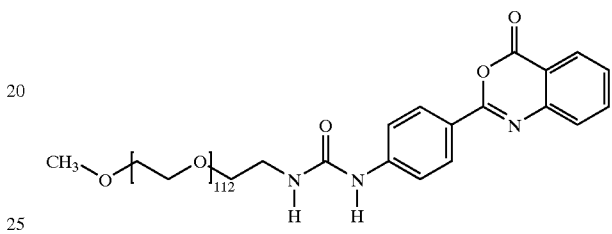

Another preferred polymer conjugate comprises a 4H-benzoxazin-4-one heterocyclic unit wherein one R unit is guanidinyl which is linked by an N-ethylene-N'-phenylene urea unit to a polyethyleneglycol polymer component having an average molecular weight of about 5000 daltons having the formula:

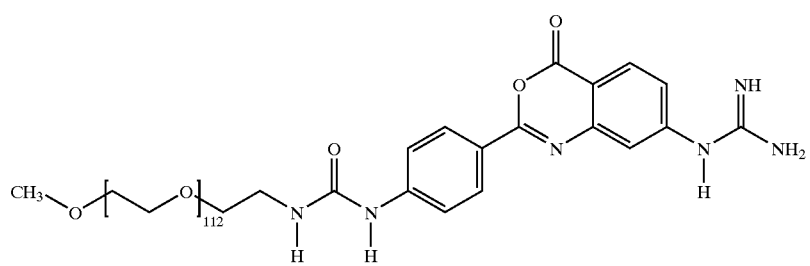

Another preferred polymer conjugate comprises a 4H-benzoxazin-4-one heterocyclic unit wherein one R unit is methyl which is linked directly to a polyethyleneglycol polymer component having an average molecular weight of about 5000 daltons having the formula:

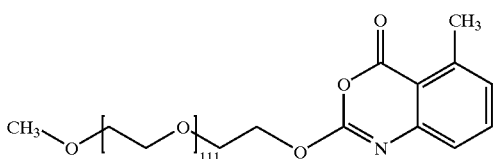

Another preferred polymer conjugate comprises a thieno[3,2-d][1,3]oxazine-4-one heterocyclic unit wherein one R unit is methyl which is linked directly to a polyethyleneglycol polymer component having an average molecular weight of about 5000 daltons having the formula

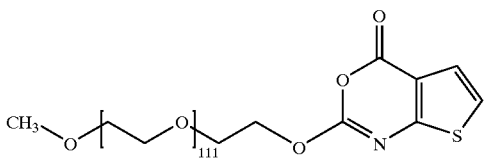

The following are non-limiting examples of polymer conjugates according to the present invention.

EXAMPLE 1

Synthesis of 2-(MPEG 5000)-5-methyl-4H-3,1-benzoxazin-4-one in dichloromethane

Methoxy polyethyleneglycol having an average molecular weight of about 5000 daltons (MPEG 5000) (50 g, 0.01 mol) is charged to a reaction vessel and dissolved in dichloromethane (125 mL). Under an inert atmosphere, a solution of phosgene in toluene (5.7 mL, 1.93 M) is added while cooling in ice. After addition, the ice bath is removed and the reaction mixture stirred for 12–18 h under an inert atmosphere to form an MPEG 5000 chloroformate. In a separate flask, 2-amino-6-methylbenzoic acid (1.66 g, 0.011 mol) is dissolved in dichloromethane (100 mL) which is heated to 30° C. The heat source is removed and while still warm, poly(N-vinylpyridine) (10.23 g, 0.09 mol) is added to the solvent. With vigorous stirring, the MPEG 5000 chloroformate is added dropwise to the mixture. The reaction mixture is stirred for 12–24 h, then ethyl chloroformate (9.6 mL, 0.1 mol) is added at room temperature and stirred for another 12–24 h. The solution is filtered to remove the poly(N-vinylpyridine) and the solution is precipitated onto 3.5 L of diethyl ether. The precipitate is filtered under nitrogen to yield 2-(MPEG 5000)-5-methyl-4H-3,1-benzoxazin-4-one as a white solid (33.3 g, 67%) which is dried under vacuum.

EXAMPLE 2

Synthesis of 2-(MPEG 5000)-5-methyl-4H-3,1-benzoxazin-4-one in toluene

Methoxy polyethyleneglycol having an average molecular weight of about 5000 daltons (MPEG 5000) (13.7 g, 2.75 mmol) is charged to a reaction vessel and dissolved in toluene (100 mL) at 48° C. Under an inert atmosphere, a solution of phosgene in toluene (1.6 mL, 1.93M) is added while cooling in ice. After the addition, the reaction mixture is stirred for 12–18 h under an inert atmosphere at 48° C. to form an MPEG 5000 chloroformate. In a separate flask, 2-amino-6-methylbenzoic acid (457 mg, 3.025 mmol) is dissolved in toluene (70 mL) that is heated to 75° C. Poly(N-vinylpyridine) (3.75 g, 0.033 mol) is added to the solution. The MPEG 5000 chloroformate is added dropwise to the anthranilate mixture. The reaction mixture is stirred for 12–24 h, then the temperature is raised to 80° C. and ethyl chloroformate (2.6 mL, 27.5 mmol) is added and reaction mixture is stirred for another 12–24 h. The solution is filtered to remove the poly(N-vinylpyridine) and the solution is precipitated onto 3.5 L of diethyl ether. The precipitate is filtered under nitrogen to yield 2-(MPEG 5000)-5-methyl-4H-3,1-benzoxazin-4-one as a white solid (12.4 g, 90%) which is dried under vacuum.

EXAMPLE 3

Synthesis of bis-2-(PEG 4000)-5-methyl-4H-3,1-benzoxazin-4-one

Polyethylene glycol having an average molecular weight of about 4000 daltons (PEG 4000) (5 g, 1.25 mmol) is charged to a reaction vessel and dissolved in dichloromethane (16 mL). Under an inert atmosphere, a solution of phosgene in toluene (1.6 mL, 1.93 M) is added. After addition, the reaction mixture is stirred for 12–18 h to form the PEG-4000 bis chloroformate. In a separate flask, 2-amino-6-methylbenzoic acid (416 mg, 2.75 mmol) is dissolved in dichloromethane (25 mL) which is warmed to 30° C. The heat source is removed and while still warm, poly(N-vinylpyridine) (2.13 g, 18.75 mmol) is added to the anthranilate solution. The MPEG bis chloroformate is added dropwise to anthranilate mixture, and the reaction mixture stirred for 12–24 h and ethyl chloroformate (1.8 mL, 18.75 mmol) is added at room temperature. The reaction mixture is stirred for 12–24 h. The solution is filtered to remove the poly(N-vinylpyridine) and the solution is precipitated onto 3.5 L of diethyl ether. The precipitate is filtered under nitrogen to yield bis-2-(PEG 4000)-5-methyl-4H-3,1-benzoxazin-4-one as a white solid (4.3 g, 86%) which is dried under vacuum.

EXAMPLE 4

Preparation of 2-N-(PEG 5000)amino4H-3,1-benzoxazine-4-one

Methyl 2-isocyanatobenzoate (0.135 g, 0.76 mmol) is combined with PEG 5000 amine (2.5 g, 0.5 mmol) in dichloromethane (5 mL) and stirred 18 hours at room temperature. The reaction mixture is diluted with diethyl ether (200 mL) and the resulting precipitate of urea is recovered by filtration.

The PEG 5000 urea from step one (2.2 g, 0.41 mol) is treated with concentrated sulfuric acid (4 mL) and allowed to stand for 4 hours. The reaction mixture is diluted with excess saturated sodium bicarbonate and held at 0° C. Extraction with dichloromethane affords the 4H-benzoxazin-4-one linked by an N-ethylene-N'-phenylene urea moiety to a polyethyleneglycol polymer component having an average molecular weight of about 5000 daltons.

EXAMPLE 5

Preparation of N-4-(7-guanidinyl-4H-3,1-benzoxazine-4-one-2-yl)phenylene N'-PEG 5000 Urea 2-(4-Amino)phenyl-7-bis(Boc)-guanidino4H-3,1-benzoxazin-4-one (0.05 g, 0.101 mmol) is combined with N-methyl-morpholine (0.011 mL, 0.1 mmol) in THF (5 mL). A solution of 4-nitrophenyl chloroformate (0.02 g, 0.1 mmol) in THF (mL) is added dropwise and the solution is stirred for 4 hours. PEG 5000 amine (0.25 g) is dissolved in THF (3 mL) and added to the reaction solution with is subsequently allowed to stand overnight. The reaction is diluted with diethyl ether (100 mL) and the resulting precipitate is collected by filtration.

The N-7- bis(Boc)-guanidino-2-(4-amino)phenyl-4H-3,1-benzoxazine-4-one-2-yl N' PEG 5000 urea from above (0.5 g, 0.1 mmol) is dissolved in glacial acetic acid (4 mL) and refluxed for 15 minutes The solvent is removed under reduced pressure to afford N-4-(7-guanidinyl-4H-3,1-benzoxazine-4-one-2-yl)phenylene N'-PEG 5000 urea.

EXAMPLE 6

Preparation of 2-PEG 5000-5-methyl-4H-3,1-benzoxazin-4-one

PEG 5000 (1 g, 0.2 mmol) is dissolved in dichloromethane (25 mL) and a solution of 12.5% phosgene in toluene (93.3 mL, 6.37 mmol) is added dropwise at room temperature. After 30 minutes the solution is diluted with diethyl ether and the PEG 5000 chloroformate precipitate is collected by filtration.

6-Methyl anthranilic acid (0.15 g, 1 mmol) is dissolved in a mixture of 1% sodium bicarbonate (2.5 mL) and THF (0.5 mL). The PEG 5000 chloroformate from above (1 g, 0.2 mmol) is dissolved in THF and added dropwise to the reaction solution and is stirred for 18 hours. The reaction solution is extracted with dichloromethane, the extracts combined and the solvent removed under reduced pressure to yield the PEG 5000/benzoxazine carbamate.

The carbamate from above (0.05 g, 0.01 mmol) is dissolved in pyridine (3 mL) and ethyl chloroformate (0.004 mL, 4.0 mmol) is added followed by activated molecular sieves. After stirring 18 hours the solvent is removed under reduced pressure to afford the desired product.

EXAMPLE 7

Preparation of 2-PEG 5000-[2,3-d]thieno[1,3] oxazin-4-one

2-Amino-3-thiophenecarboxylic acid (0.129 g, 1 mmol) is dissolved in 1% sodium bicarbonate (2.5 mL) and THF (0.5 mL). The PEG 5000 chloroformate from above (1 g, 0.2 mmol) is dissolved in THF and added dropwise to the reaction solution and is stirred for 18 hours. The reaction solution is extracted with dichloromethane, the extracts combined and the solvent removed under reduced pressure to afford the thiophenecarboxylic acid carbamate.

An admixture of trifluoroacetic acid (1 mL) and trifluoroacetic anhydride (0.0147 g, 0.07 mmol) are combined and cooled to 0° C. to which is added portionwise over 30 minutes the thiophenecarboxylic acid carbamate (0.25 g, 0.05 mmol). After 90 minutes the solution is diluted with diethyl ether and the resulting 2-PEG 5000-[2,3-d]thieno[1,3]-oxazin-4-one precipitate is collected by filtration.

The polymer conjugates of the present invention are effective in treating and/or preventing one or more skin conditions, including irritation, resulting from the contact of enzymes with skin, inter alia, diaper rash. One effective means for delivering the stable conjugates to skin is via an article of manufacture, preferably an "absorbent article". Non-limiting examples of absorbent articles include sanitary napkins, panty liners, diapers, incontinence briefs, training briefs.

Typically the polymer conjugates of the present invention are formulated into a skin-compatible carrier which serves to solublize the conjugate in addition to providing a vehicle for uniform delivery of the enzyme inhibitor to the skin surface. The formulator of articles of manufacture which employ the enzyme inhibiting conjugates of the present invention will recognize the vehicle may take any form, inter alia, aqueous, non-aqueous, dry powder.

The amount of polymer conjugate which is present in the formulation depends upon the embodiment chosen by the formulator. In some instances, the polymer component of the conjugate itself may have properties which allow for the direct application of the conjugate without the need for a vehicle. However, when incorporated as part of a composition, the conjugate will comprise from about 0.01%, preferably from about 1% to about 20%, preferably to about 10% by weight, of the delivery vehicle.

The following are non-limiting examples of assays which may be used to determine the effective levels of the polymer conjugates of the present invention.

Fecal Protease Inhibition Assay

By way of illustration, to determine the activity of fecal protease inhibiting compounds, the compounds of the present invention may be tested in a standard enzyme assay for protease activity, as follows:

Infant feces are collected in a manner to keep them free from urine contamination and mixed with water to obtain a weight by weight (w/w) mixture (e.g., 1:4 w/w). This mixture is then mixed thoroughly to obtain a homogeneous suspension by homogenization or sonication. The feces are then diluted with a reaction buffer, described below, to obtain a fecal concentration which, when added to a protease substrate, hydrolyzes the substrate over a 5 to 60 minute period. Using such a method, for example, fecal trypsin activity may be determined at pH 8.2 in a 50 nM Tris-HCl buffer with 20 mM $CaCl_2$, containing 0.3 mM of the composition to be tested; fecal chymotrypsin activity at pH 7.6 in a 50 mM Tris-HCl buffer with 20 mM $CaCl_2$, containing 0.05 mM of the composition to be tested; and fecal leucine aminopeptidase activity at pH 7.2 in 50 mM sodium phosphate containing the composition to be tested. To test the efficacy of the compositions, several different concentrations of each putative inhibitory composition are added to duplicate feces-containing reaction buffers, and the inhibition of the enzyme activity is measured. Compounds having an $IC_{50}$ of 100 $\mu$M or less are preferred compounds of the invention. More preferred are compounds having an $IC_{50}$ to $IC_{90}$, and most preferably an $IC_{80}$ to $IC_{90}$, of 100 $\mu$M or less.

In Vitro Skin Test for Inhibition of IL-1α Production

An in vitro method to determine the efficacy of the compounds of the present invention in preventing the proinflammatory response of the skin to feces and fecal enzymes may be performed as follows:

Human keratinocytes are obtained from epidermal tissue and cultured in serum-free medium in plastic culture vessels containing a nylon mesh surface for a period of time until they are confluent. The mesh surface is then raised to the liquid air interface in order to promote differentiation and formation of multilayered organized layers analogous to those found in vivo, including a well defined stratum corneum barrier. Any cell culture system that promotes the growth and differentiation of keratinocytes, as described, may be employed. A commercially available cell culture system suitable for use is Epiderm® (MatTek Corporation).

Infant feces are collected in a manner to keep them free of urine contamination and diluted with phosphate-buffered saline (PBS) (pH 7.2–7.4). The mixture is then mixed thoroughly to obtain a homogenous suspension by homogenization or sonication. To assay for IL-1α production due to fecal enzyme activity, an aliquot of the homogenate is diluted with PBS and added to the surface of a control culture in a culture vessel. To assay for inhibition of IL-1α production due to protease activity, a predetermined quantity of a putative inhibitor (compound) is added to an otherwise identical diluted aliquot of the homogenate prior to adding it to the surface of a test culture. The cultures are allowed to incubate in a controlled atmosphere. At selected times, the control cultures and inhibitor-treated test cultures, and the underlying culture media are harvested. The culture media are assayed for the presence of IL-1α by known methods. For example, a suitable assay for IL-1α is an enzyme-linked immunoabsorbent method commercially available as Quantikine® from R&D Systems.

The percent reduction in IL-1α production due to the presence of the compound (inhibitor) is calculated as follows:

$$\% \text{ Reduction} = \left[ \frac{(IL-1_\alpha \text{ from control culture}) - (IL-1_\alpha \text{ from test culture})}{(IL-1_\alpha \text{ from control culture})} \right] \times 100$$

The polymer conjugates of the present invention are effective in treating and/or preventing one or more skin conditions, including irritation, resulting from the contact of enzymes with skin, inter alia, diaper rash. One effective means for delivering the stable conjugates to skin is via an article of manufacture, preferably an "absorbent article". Non-limiting examples of absorbent articles include sanitary napkins, panty liners, diapers, incontinence briefs, training briefs.

Adjunct Biologically Active Ingredients

The formulator can add to the compositions of the present invention one or more "adjunct biologically active ingredients" to adjust the properties of the composition or to serve as an aid, inter alia, for healing of skin, increase enzyme inhibition.

A non-limiting example of a biologically active adjunct ingredient is hexamidine, 4,4'-[1,6-hexanediylbis(oxy)] bisbenzenecarboximidamide. Hexamidine is preferred as an adjunct to the polymer conjugates of the present invention. Without being limited by theory or application, hexamidine has multiple properties ascribed thereto, inter alia, as a topical antiseptic: *Bordeaux Med.*, M. J. Fénelon, 3, 867 (1970); as an antibacterial: *J. Int. Med. Res.*, G. Micheal et al., 14, 205 (1986). Hexamidine is preferably delivered as the diisethionate as Elestab HP 100® available ex Rhone-Poulenc; inter alia, as RF 2535, Desomedine, Esomedine, Hexomedine, Ophtamedine.

Formulations

For topical administration to the epidermis, the conjugates of the present invention may be formulated as ointments, creams, lotions, etc. which can be directly applied or delivered via an article of manufacture, inter alia, a diaper, facial tissue. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, preservatives, emollients, skin conditioning agents, or colorizing agents.

Typically the polymer conjugates of the present invention are formulated into a skin-compatible carrier which serves to solublize the conjugate in addition to providing a vehicle for uniform delivery of the enzyme inhibitor to the skin surface. The formulator of articles of manufacture which employ the enzyme inhibiting conjugates of the present invention will recognize the vehicle may take any form, inter alia, aqueous, non-aqueous, dry powder.

The amount of polymer conjugate which is present in the formulation depends upon the embodiment chosen by the formulator. In some instances, the polymer component of the conjugate itself may have properties which allow for the direct application of the conjugate without the need for a vehicle. However, when incorporated as part of a composition, the conjugate will typically comprise from about 0.01%, preferably from about 1% to about 20%, preferably to about 10% by weight, of the delivery vehicle.

The compositions of the present invention will preferably comprise one or more adjunct ingredients which include carriers. For the purposes of the present invention the term "carriers" is used interchangeably with the term "emollients", "lotion base", etc. The formulator will recognize that certain carriers will have an emollient property or can serve more than one function. The compositions of the present invention comprise from about 1%, preferably from about 5%, more preferably from about 10% to about 99%, preferably to about 95%, more preferably to about 80%, most preferably to about 50% by weight, of one or more carriers. Non-limiting examples of carriers include petroleum-based emollients, sucrose ester fatty acids, polyethylene glycol and derivatives thereof, humectants, fatty acid ester type, alkyl ethoxylate type, fatty acid ester ethoxylates, fatty alcohol type, polysiloxane type, propylene glycol and derivatives thereof, glycerin and derivatives thereof, including glyceride, acetoglycerides, and ethoxylated glycerides of $C_{12}$–$C_{22}$ fatty acids, triethylene glycol and derivatives thereof, spermaceti or other waxes, fatty acids, fatty alcohol ethers, propoxylated fatty alcohols, other fatty esters of polyhydroxy alcohols, lanolin, kaolin, any of the Federally monographed commercially available skin care. Suitable petroleum-based emollients include $C_{16}$–$C_{32}$ hydrocarbons, including paraffins, include mineral oil and petrolatum (also known as "mineral wax", "petroleum jelly", and "mineral jelly").

The balance of the compositions of the present invention typically comprises, other than carriers, other adjunct ingredients. Non limiting examples of other preferred adjunct ingredients include water, viscosity modifiers, perfumes, disinfectant antibacterial actives, antiviral agents, vitamins, pharmaceutical actives, film formers, deodorants, opacifiers, astringents, solvents, preservatives, viscosity modifiers, and mixtures thereof. In addition, stabilizers can be added to enhance the shelf life of the composition such as cellulose derivatives, proteins, lecithin, anti-oxidants, and sequestrants.

Water-based skin care carriers and compositions may optionally comprise a preservative, non-limiting examples of which include propyl paraben, methyl paraben, butyl paraben, benzyl alcohol, benzalkonium chloride, tribasic calcium phosphate, BHT, or acids such as citric, tartaric, maleic, lactic, malic, benzoic, salicylic, and mixtures thereof.

A preferred use of the polymer conjugates of the present invention is for treatment or prevention of skin irritation from exposure to human feces as it relates to diaper rash and other articles of manufacture used to contain human waste. The polymer conjugates of the present invention inhibit proteolytic and/or lipolytic enzymes whether endogenous or exogenous. Therefore the formulator can employ the conjugates of the present invention in any embodiment which has the purpose of modulating or preventing the effects of exposure to said enzymes. However, the formulations can have a variety of other uses, non-limiting examples of which include applying the compositions to cotton swabs wherein the compositions are applied to area where enzyme activity is to be inhibited or modulated (i.e., nasal canal, throat), applying the compositions to facial tissues or wipes for application to any skin surface or orifice, inter alia, nasal passage, ocular region.

The following are non-limiting examples of compositions according to the present invention:

A composition for inhibiting enzymes on human skin comprising:

a) from about 0.01%, preferably from about 0.5%, more preferably from about 1%, most preferably from about 1.5% to about 10%, preferably to about 7.5%, more preferably to about 5% by weight, of one or more polymer conjugates which are capable of inhibiting one or more proteolytic enzymes having the formula:

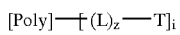

wherein T is a heterocyclic unit; L is a linking group; [Poly] is a polymeric unit, i indicates the number of said heterocyclic units which comprise said conjugate and has the value of from 1 to 100; z is 0 or 1; and b) the balance carriers and adjunct ingredients.

A composition for application to human skin, said composition inhibiting proteolytic and/or lipolytic enzymes on human skin comprising:

a) from about 0.01%, preferably from about 0.5%, more preferably from about 1%, most preferably from about 1.5% to about 10%, preferably to about 7.5%, more preferably to about 5% by weight, of one or more polymer conjugates unit which are capable of inhibiting one or more proteolytic enzymes having the formula:

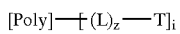

wherein T is a heterocyclic; L is a linking group; [Poly] is a polymeric unit, i indicates the number of said heterocyclic units which comprise said conjugate and has the value of from 1 to 100; z is 0 or 1;

b) from about 0.01%, preferably from about 0.05%, more preferably from about 0.1% to about 5%, preferably to about 2%, more preferably to about 1% by weight, of an adjunct biologically active ingredient, preferably hexamidine; and c) the balance carriers and adjunct ingredients.

A composition for application to human skin, said composition inhibiting proteolytic and/or lipolytic enzymes on human skin comprising:

a) from about 0.01%, preferably from about 0.5%, more preferably from about 1%, most preferably from about 1.5% to about 10%, preferably to about 7.5%, more preferably to about 5% by weight, of one or more polymer conjugates having the formula:

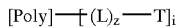

wherein T is a heterocyclic unit which is capable of inhibiting one or more proteolytic enzymes; L is a linking group; [Poly] is a polymeric unit, i indicates the number of said heterocyclic units which comprise said conjugate and has the value of from 1 to 100; z is 0 or 1;

b) from about 0.01%, preferably from about 0.05%, more preferably from about 0.1% to about 5%, preferably to about 2%, more preferably to about 1% by weight, of hexamidine;

c) from about 0.01% by weight, of a carrier alcohol, preferably a $C_{10}$–$C_{20}$ linear or branched, saturated or unsaturated alkyl alcohol;

d) from about 0.01% by weight, of a secondary benefit agent, preferably selected from the group consisting of vitamins, sun screens, depilatories, desiccants, astringents, and mixtures thereof;

e) from about 0.01% by weight, of an aesthetic, said aesthetic selected from the group consisting of perfumes, fragrances, dyes, colorants, and mixtures thereof; and f) the balance carriers and emollients, said adjunct ingredients selected from the group consisting of petroleum-based emollients, sucrose ester fatty acids, polyethylene glycol and derivatives thereof, humectants, fatty acid esters, alkyl ethoxylates, fatty acid ester ethoxylates, fatty alcohols, polysiloxanes, propylene glycol and derivatives thereof, glycerin, glyceride, acetoglycerides, and ethoxylated glycerides of $C_{12}$–$C_{22}$ fatty acids, triethylene glycol and derivatives thereof, waxes, fatty acids, fatty alcohol ethers, propoxylated fatty alcohols, fatty esters of polyhydroxy alcohols, lanolin, kaolin, and mixtures thereof.

A composition for inhibiting enzymes on human skin comprising:

a) from about 0.01%, preferably from about 1% to about 20%, preferably to about 10% by weight, of one or more polymer conjugates which are capable of inhibiting one or more proteolytic enzymes having the formula:

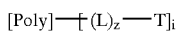

wherein T is a heterocyclic unit; L is a linking group; [Poly] is a polymeric unit, i indicates the number of said heterocyclic units which comprise said conjugate and has the value of from 1 to 100; z is 0 or 1; and b) the balance a delivery vehicle.

The following are non-limiting examples of a composition comprising a polymer conjugate according to the present invention which is suitable for use in an absorbent article.

EXAMPLE 8

| Ingredients | % |
|---|---|
| Petrolatum[1] | 52.2 |
| Stearyl alcohol[2] | 36.9 |
| Aloe[3] | 0.9 |
| Polymer conjugate[4] | 10.0 |
| Carriers | balance |

[1]White Protopet ® available ex Witco.
[2]CO 1897 available ex Procter & Gamble.
[3]Veragel Lipid in Kaydol available ex Madis Botanicals.
[4]Enzyme inhibitor according to Example 1.

TABLE I

| | weight % | |
|---|---|---|
| Ingredients | 9 | 10 |
| Petrolatum[1] | 71.2 | 58.9 |
| Behenyl alcohol | 17.4 | 24 |
| Beheneth-10 | 6.3 | 12 |
| Fumed Silica, NF | 2.0 | 3.6 |
| Polymer conjugate[2] | 1.0 | 1.0 |

TABLE I-continued

| Ingredients | weight % 9 | 10 |
| --- | --- | --- |
| Hexamidine diisethionate | 0.1 | 0.1 |
| Tocopherol acetate | 0.5 | 0.1 |
| Chamomile | 0.5 | 0.1 |
| Aloe | 0.5 | 0.1 |
| Lanolin | 0.5 | 0.1 |
| Carriers | balance | balance |

[1]White Protopet ® available ex Witco.
[2]Enzyme inhibitor according to Example 1.

The compositions of the present invention can also be delivered to skin via compositions which provide other primary benefits. The following disclose compositions which can incorporate the enzyme inhibiting polymer conjugates of the present invention and are each incorporated herein by reference.

Skin Cleansers

U.S. Pat. No. 5,641,479, Linares et al., issued Jun. 24, 1997; U.S. Pat. No. 5,599,549, Wivell et al., issued Feb. 4, 1997; U.S. Pat. No. 5,585,104, Ha et al., issued Dec. 17, 1996; U.S. Pat. No. 5,540,852, Kefauver et al., issued Jul. 30, 1996; and U.S. Pat. No. 5,510,050, Dunbar et al., issued Apr. 23, 1996.

Facial Acne Preparations

U.S. Pat. No. 5,612,324, Guang Lin et al., issued Mar. 18, 1997; U.S. Pat. No. 5,587,176, Warren et al., issued Dec. 24, 1996; U.S. Pat. No. 5,549,888, Venkateswaran, issued Aug. 27, 1996; and U.S. Pat. No. 5,470,884, Corless et al., issued November 28, 1995.

Shower Gels

U.S. Pat. No. 5,650,384, Gordon et al., issued Jul. 22, 1997; and U.S. Pat. No. 5,607,678, Moore et al., issued Mar. 4, 1997.

Cosmetics

U.S. Pat. No. 5,641,493, Date et al., issued Jun. 24, 1997; U.S. Pat. No. 5,605,894, Blank et al., issued Feb. 25, 1997; U.S. Pat. No. 5,585,090, Yoshioka et al., issued Dec. 17, 1996.

Hand, Face, and Body Lotions

U.S. Pat. No. 4,939,179, Cheney et al., issued Jul. 3, 1990; and U.S. Pat. No. 5,607,980, McAtee et al., issued Mar. 4, 1997.

Cosmetic and Cleansing Wipes

U.S. Pat. No. 4,045,364, Richter et al., issued Aug. 30, 1977; European Patent Application, EP 0 619 074, Touchet et al., published Oct. 12, 1994; U.S. Pat. No. 4,975,217, Brown-Skrobot et al., issued Dec. 4, 1990; U.S. Pat. No. 5,043,155, Puchalski et al., issued Aug. 27, 1991; and U.S. Pat. No. 5,648,083, Blieszner et al., issued Jul. 15, 1997.

METHOD OF USE

The present invention also comprises a method for the treatment and prevention of diaper rash and diaper dermatitis caused by the prolonged contact of human skin with body waste. The present invention also ameliorates and serves as a prophylactic means to prevent the occurrence of said skin irritation by providing a barrier against unwanted protease or lipase enzymes.

The method of the present invention comprises the step of contacting human skin with a composition comprising:

a) an effective amount, preferably from about 0.1%, more preferably from about 1% by weight, of a polymer conjugate according to the present invention; and b) the balance carriers and adjunct ingredients;

wherein said composition is optionally, but preferably, applied to a substrate, inter alia, diaper topsheet, sanitary napkin. The methods of the present invention are carried out a pH which is compatible with the skin of the user.

Preferably the methods of the present invention also include contacting human skin with an ingredient which provides an additional benefit to the user, inter alia, provides conditioning to the exposed skin.

Normally the methods of the present invention deliver an "effective amount" of the compositions, which is the minimum inhibitory concentration of the selected enzyme inhibitor, to the skin. However, depending upon the formulation and the means for performing the methods of the present invention, any amount may be delivered by the formulator.

What is claimed is:

1. A composition for inhibiting enzymes comprising:

a) from about 0.01% by weight, of one or more polymer conjugates capable of inhibiting one or more proteolytic enzymes having the formula:

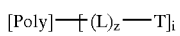

wherein T has a formula selected from the group consisting of:

i)

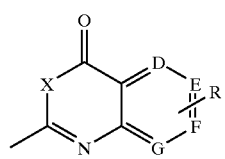

ii)

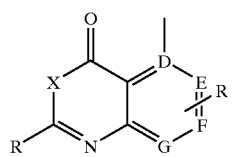

iii)

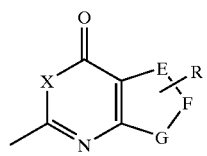

iv)

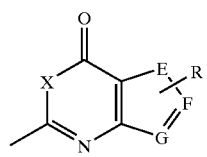

v)

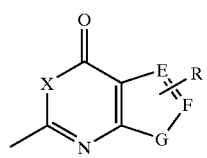

vi)

-continued vii) 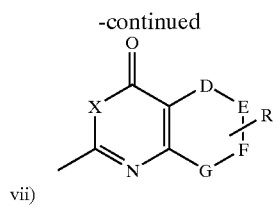

viii) 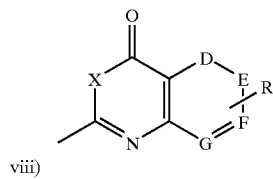

ix) 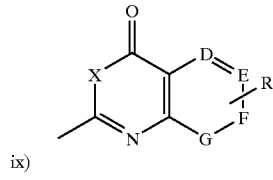

x) 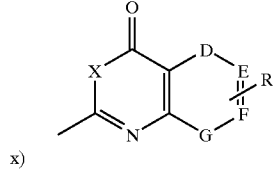

xi) 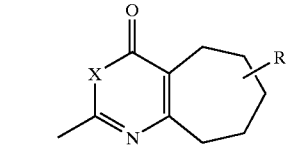

and mixtures thereof;
wherein X is selected from the group consisting of —CH$_2$—, —NH—, —O—, —S—, —CF$_2$—, and mixtures thereof; and each D, E, F, and G is independently selected from the group consisting of —CH—, —CH$_2$—, —N—, —NH—, —O—, —S—, —CF$_2$—, and mixtures thereof;
a) hydrogen;
b) C$_1$–C$_{18}$ substituted or unsubstituted, linear or branched alkyl;
c) C$_3$–C$_{18}$ substituted or unsubstituted, linear or branched cycloalkyl;
d) C$_2$–C$_{18}$ substituted or unsubstituted, linear or branched alkenyl;
e) C$_2$–C$_{18}$ substituted or unsubstituted, linear or branched alkynyl;
f) C$_6$–C$_{18}$ substituted or unsubstituted aryl;
g) C$_2$–C$_{18}$ substituted or unsubstituted heterocyclic alkyl;
h) C$_3$–C$_{18}$ substituted or unsubstituted heterocyclic alkenyl;
i) alkylenearyl having the formula:

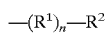

wherein R$^1$ is C$_1$–C$_{12}$ linear or branched alkylene, C$_2$–C$_{12}$ linear or branched alkenylene, or mixtures thereof; R$^2$ C$_6$–C$_{18}$ substituted or unsubstituted aryl, or mixtures thereof; n is from 1 to 16;
j) an amino unit having the formula:

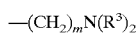

wherein each R$^3$ is independently C$_1$–C$_{18}$ substituted or unsubstituted, linear or branched alkyl; m is from 0 to 10;
k) a quaternary ammonium unit having the formula:

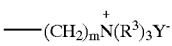

wherein each R$^3$ is independently C$_1$–C$_{18}$ substituted or unsubstituted, linear or branched alkyl; Y is an anion of sufficient charge to provide electronic neutrality; m is from 0 to 10;
l) a unit having the formula:

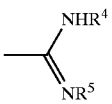

wherein R$^4$ is hydrogen, C$_1$–C$_4$ alkyl, or mixtures thereof; R$^5$ is hydrogen, C$_1$–C$_4$ alkyl, or mixtures thereof; R$^4$ and R$^5$ can be taken together to form a heterocyclic ring comprising from 3 to 5 carbon atoms;
m) a unit having the formula:

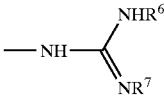

wherein R$^6$ is hydrogen, C$_1$–C$_4$ alkyl, or mixtures thereof; R$^7$ is hydrogen, C$_1$–C$_4$ alkyl, or mixtures thereof; R$^6$ and R$^7$ can be taken together to form a heterocyclic ring comprising from 3 to 5 carbon atoms;
n) a unit having the formula:

wherein R$^8$ is:
i) —(CH$_2$)$_p$—, wherein p is from 0 to 12;
ii) —C(O)—;
iii) —C(X)NR$^{10}$—, wherein R$^{10}$ is hydrogen, C$_1$–C$_4$ alkyl, or mixtures thereof; X is oxygen, sulfur, NR$^{10}$, and mixtures thereof;
iv) —C(X)R$^{11}$C(X)—, wherein R$^{11}$ is C$_1$–C$_{18}$ alkylene, substituted or unsubstituted phenylene. or mixtures thereof; X is oxygen, sulfur, NR$^{10}$, and mixtures thereof;
v) —C(X)NR$^{10}$C(X)—, wherein R$^{10}$ is hydrogen, C$_1$–C$_4$ alkyl, or mixtures thereof; X is oxygen, sulfur, NR$^{10}$, and mixtures thereof;
vi) —C(X)NR$^{10}$R$^{11}$NR$^{10}$C(X)—, wherein R$^{10}$ is hydrogen, C$_1$–C$_4$ alkyl, or mixtures thereof; R$^{11}$ is C$_1$–C$_{12}$ alkylene, substituted or unsubstituted phenylene, or mixtures thereof; X is oxygen, sulfur, NR$^{10}$, and mixtures thereof;
vii) —NR$^{10}$C(X)—, wherein R$^{10}$ is hydrogen, C$_1$–C$_4$ alkyl, or mixtures thereof; X is oxygen, sulfur, NR$^{10}$, and mixtures thereof;
viii) —NR$^{10}$C(X)NR$^{10}$—, wherein R$^{10}$ is hydrogen, C$_1$–C$_4$ alkyl, or mixtures thereof; X is oxygen, sulfur, NR$^{10}$, and mixtures thereof;
ix) —NR$^{10}$C(X)R$^{11}$NR$^{10}$—, wherein R$^{10}$ is hydrogen, C$_1$–C$_4$ alkyl, or mixtures thereof; R$^{11}$ is C$_1$–C$_{12}$ alkylene, substituted or unsubstituted phenylene, or mixtures thereof; X is oxygen, sulfur, $NR^{10}$, and mixtures thereof;

x) $-NR^{10}R^{11}C(X)NR^{10}-$, wherein $R^{10}$ is hydrogen, $C_1$–$C_4$ alkyl, or mixtures thereof; $R^{11}$ is $C_1$–$C_{12}$ alkylene, substituted or unsubstituted phenylene, or mixtures thereof; x is oxygen, sulfur, $NR^{10}$, and mixtures thereof;

xi) $-NR^{10}C(X)R^{11}C(X)O-$, wherein $R^{10}$ is hydrogen, $C_1$–$C_4$ alkyl, or mixtures thereof; $R^{11}$ is $C_1$–$C_{12}$ alkylene, substituted or unsubstituted phenylene, or mixtures thereof; X is oxygen, sulfur, $NR^{10}$, and mixtures thereof;

xii) $-OC(X)R^{11}C(X)NR^{10}-$, wherein $R^{10}$ is hydrogen, $C_1$–$C_4$ alkyl, or mixtures thereof; $R^{11}$ is $C_1$–$C_{12}$ alkylene, substituted or unsubstituted phenylene, or mixtures thereof; X is oxygen, sulfur, $NR^{10}$, and mixtures thereof;

xiii) $-NR^{10}C(X)NR^{10}R^{11}-$, wherein $R^{10}$ is hydrogen, $C_1$–$C_4$ alkyl, or mixtures thereof; $R^{11}$ is $C_1$–$C_{12}$ alkylene, substituted or unsubstituted phenylene, or mixtures thereof; X is oxygen, sulfur, $NR^{10}$, and mixtures thereof;

xiv) $-R^{11}NR^{10}C(X)NR^{10}-$, wherein $R^{10}$ is hydrogen, $C_1$–$C_4$ alkyl, or mixtures thereof; $R^{11}$ is $C_1$–$C_{12}$ alkylene, substituted or unsubstituted phenylene, or mixtures thereof; wherein X is oxygen, sulfur, $NR^{10}$, and mixtures thereof;

xv) $-R^{11}NR^{10}C(X)NR^{10}R^{11}-$, wherein $R^{10}$ is hydrogen, $C_1$–$C_4$ alkyl, or mixtures thereof; $R^{11}$ is $C_1$–$C_{12}$ alkylene, substituted or unsubstituted phenylene, or mixtures thereof; wherein X is oxygen, sulfur, $NR^{10}$, and mixtures thereof;

xvi) $-NR^{10}$, wherein $R^{10}$ is hydrogen, $C_1$–$C_4$ alkyl, or mixtures thereof;

xvii) $-O-$;

xviii) $-(R^{11})_tC(X)(R^{11})_t-$; wherein $R^{11}$ is $C_1$–$C_{12}$ alkylene, substituted or unsubstituted phenylene, or mixtures thereof; t is 0 or 1; X is oxygen, sulfur, $NR^{10}$, and mixtures thereof;

xix) $-(R^{11})_tOC(O)(R^{11})_t-$; wherein $R^{11}$ is $C_1$–$C_{12}$ alkylene, substituted or unsubstituted phenylene, or mixtures thereof; t is 0 or 1;

xx) $-R^{11})_tC(O)O(R^{11})_t-$; wherein $R^{11}$ is $C_1$–$C_{12}$ alkylene, substituted or unsubstituted phenylene, or mixtures thereof; t is 0 or 1;

xxi) alkyleneoxyalkylene having the formula:

$-(R^{12}O)_qR^{13}-$ wherein $R^{12}$ is $C_2$–$C_6$ linear or branched alkylene, substituted or unsubstituted phenylene; $R^{13}$ is $-(CH_2)_p-$, wherein p is from 0 to 12; q is from 1 to 4;

xxii) $-S-$;

xxiii) $-(R^{11})_tS(R^{11})_t-$; wherein $R^{11}$ is $C_1$–$C_{12}$ alkylene, substituted or unsubstituted phenylene, or mixtures thereof; t is 0 or 1;

xxiv) $-(R^{11})_tS(O)(R^{11})_t-$; wherein $R^{11}$ is $C_1$–$C_{12}$ alkylene, substituted or unsubstituted phenylene, or mixtures thereof; t is 0 or 1;

xxv) $-(R^{11})_tSO_2(R^{11})_t-$; wherein $R^{11}$ is $C_1$–$C_{12}$ alkylene, substituted or unsubstituted phenylene, or mixtures thereof; t is 0 or 1;

xxvi) or mixtures thereof;

$R^9$ is:
  i) hydrogen;
  ii) $C_1$–$C_{18}$ substituted or unsubstituted, linear or branched alkyl;
  iii) $C_3$–$C_{18}$ substituted or unsubstituted, linear or branched cycloalkyl
  iv) $C_2$–$C_{18}$ substituted or unsubstituted, linear or branched alkenyl;
  v) $C_2$–$C_{18}$ substituted or unsubstituted, linear or branched alkynyl;
  vi) $C_6$–$C_{18}$ substituted or unsubstituted aryl;
  vii) $C_2$–$C_{18}$ substituted or unsubstituted heterocyclic alkyl;
  viii) $C_3$–$C_{18}$ substituted or unsubstituted heterocyclic alkenyl;
  ix) $-OH$;
  x) $-SO_3M$;
  xi) $-OSO_3M$;
  xii) $-NO_2$;
  xiii) halogen selected from fluorine, chlorine, bromine, iodine, or mixtures thereof;
  xiv) $-C(Hal)_3$, wherein each Hal is fluorine, chlorine, bromine, iodine, or mixtures thereof;
  xv) $-COR^{14}$; wherein $R^{14}$ is hydrogen, $-OH$, $C_1$–$C_{12}$ alkyl, $C_1$–$C_{12}$ alkoxy, or mixtures thereof; $-N(R^{15})_2$, or mixtures thereof; each $R^{15}$ is independently hydrogen, $-OH$, $C_1$–$C_4$ alkyl, or mixtures thereof;
  xvi) $-CH(OR^{14})_2$ wherein $R^{14}$ is hydrogen, $C_1$–$C_{12}$ alkyl, or two $R^{14}$ units can be taken together to form a ring having from 3 to 5 carbon atoms; or mixtures thereof;
  xvii) a unit having the formula:

$$\diagup\!\!\!\!\diagdown\begin{array}{c}NHR^4\\NR^5\end{array}$$

wherein $R^4$ is hydrogen, $C_1$–$C_4$ alkyl, or mixtures thereof; $R^5$ is hydrogen, $C_1$–$C_4$ alkyl, or mixtures thereof; $R^4$ and $R^5$ can be taken together to form a heterocyclic ring comprising from 3 to 5 carbon atoms;

xviii) a unit having the formula:

$$-NH-\!\!\diagup\!\!\!\!\diagdown\begin{array}{c}NHR^6\\NR^7\end{array}$$

wherein $R^6$ is hydrogen, $C_1$–$C_4$ alkyl, or mixtures thereof; $R^7$ is hydrogen, $C_1$–$C_4$ alkyl, or mixtures thereof; $R^6$ and $R^7$ can be taken together to form a heterocyclic ring comprising from 3 to 5 carbon atoms;

xix) $-NHOR^{16}$, wherein $R^{16}$ is hydrogen; $C_1$–$C_{12}$ linear or branched alkyl; acyl having the formula $-COR^{17}$, wherein $R^{17}$ is $C_1$–$C_4$ alkyl; or mixtures thereof;

xx) a unit having the formula:

$-CH=NOR^{16}$ wherein $R^{16}$ is hydrogen; $C_1$–$C_{12}$ linear or branched alkyl; $C_7$–$C_{22}$ linear or branched alkylenearyl; acyl having the formula $-COR^{17}$, $R^{17}$ is $C_1$–$C_4$ alkyl; or mixtures thereof;

xxi) an amino unit having the formula:

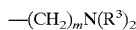
—(CH$_2$)$_m$N(R$^3$)$_2$ wherein each R$^3$ is independently C$_1$–C$_{18}$ substituted or unsubstituted, linear or branched alkyl; m is from 0 to 10;

xxii) a quaternary ammonium unit having the formula:

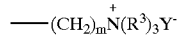
—(CH$_2$)$_m$N$^+$(R$^3$)$_3$Y$^-$ wherein each R$^3$ is independently C$_1$–C$_{18}$ substituted or unsubstituted, linear or branched alkyl; Y is an anion of sufficient charge to provide electronic neutrality; m is from 0 to 10;

o) two R units on the same carbon atom can be taken together to form a carbonyl unit or carbonyl unit equivalent; and p) mixtures thereof;

L is a linking group; [Poly] is a polymeric unit, i indicates the number of said heterocyclic units which comprise said conjugate and has the value of from 1 to 100;

z is 0 or 1; and b) the balance carriers and adjunct ingredients.

2. A composition according to claim 1, herein each R is independently:
a) hydrogen;
b) C$_1$–C$_8$ linear unsubstituted alkyl;
c) C$_6$–C$_{10}$ unsubstituted cycloalkyl;
d) C$_{10}$ and C$_{15}$ branched alkenyl;
e) aryl units selected from the group consisting of phenyl, naphthyl, 4-methoxyphenyl, 4-nitrophenyl, 4-(C$_1$–C$_4$ alkyl)phenyl, and mixtures thereof;
f) C$_4$–C$_6$ substituted or unsubstituted heterocyclic alkyl;
g) C$_3$–C$_{18}$ substituted or unsubstituted heterocyclic alkenyl;
h) alkylenearyl having the formula:

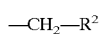
—CH$_2$—R$^2$ wherein R$^2$ is selected from the group consisting of phenyl, substituted phenyl, pyridinyl, substituted pyridinyl, and mixtures thereof;

i) an amino unit having the formula:

—N(R$^3$)$_2$ wherein each R$^3$ is independently hydrogen, methyl, ethyl, 2-hydroxyethyl, cyclopropyl, or mixtures thereof;

j) a unit having the formula:

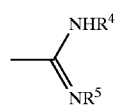

wherein R$^4$ and R$^5$ are each hydrogen, or R$^4$ and R$^5$ is taken together to form a heterocyclic ring comprising from 3 to 5 carbon atoms;

k) a unit having the formula:

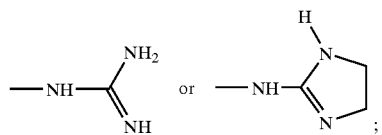

l) a unit having the formula:

—R$^8$—R$^9$ wherein R$^8$ is:
i) —(CH$_2$)$_p$—, wherein p is from 0 to 12;
ii) —C(O)—;
iii) —NR$^{10}$—, wherein R$^{10}$ is hydrogen, C$_1$–C$_4$ alkyl, or mixtures thereof;
iv) —O—;
v) alkyleneoxyalkylene having the formula:

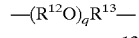
—(R$^{12}$O)$_q$R$^{13}$— wherein R$^{12}$ is C$_2$–C$_6$ linear or branched alkylene, substituted or unsubstituted phenylene; R$^{13}$ is —(CH$_2$)$_p$—, wherein p is from 0 to 12; q is from 1 to 4;
vi) —S—;
vii) or mixtures thereof;

R$^9$ is:
i) an alkyl unit selected from methyl, ethyl, propyl, isopropyl, n-butyl, isobutyl;
ii) a cycloalkyl unit selected from cyclopentyl, cyclohexyl, 4-methylcyclohexyl, 2,5dimethylcyclopentyl;
iii) an aryl unit selected from phenyl, 4-methoxyphenyl, 4-nitrophenyl, 3-chlorophenyl, 4-chlorophenyl, 3,5-dichlorophenyl, 4-aminobenzyl, 4-guanidiobenzyl;
iv) a heterocyclic unit selected from N-aziridinyl, 2-pyrrolindinyl, 3-pyrrolidinyl, 2-piperidinyl, 3-piperidinyl, 4-piperidinyl;
v) —OH, when the index p is from 1 to 4;
vi) —SO$_3$M when the index p is from 1 to 4;
vii) —OSO$_3$M when the index p is from 2 to 4;
viii) —NO$_2$;
ix) chlorine, bromine, or mixtures thereof;
x) —CF$_3$;
xi) —COR$^{14}$; wherein R$^{14}$ is —OH, —NH$_2$, —N(CH$_3$)$_2$, or mixtures thereof;
xii) —NHOR$^{16}$, wherein R$^{16}$ is hydrogen; C$_1$–C$_{12}$ linear or branched alkyl; acyl having the formula —COR$^{17}$, wherein R$^{17}$ is C$_1$–C$_4$ alkyl; or mixtures thereof;
xiii) a unit having the formula:

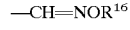
—CH=NOR$^{16}$ wherein R$^{16}$ is hydrogen or methyl; and
m) mixtures thereof.

3. A composition according to claim 2 wherein R is:
a) hydrogen;
b) an alkyl unit selected from the group consisting of methyl, ethyl, propyl, isopropyl, n-butyl, t-butyl, n-pentyl, isopentyl, n-hexyl, 2-methyl hexyl, 2-ethyl, hexyl, and mixtures thereof;
c) a cycloalkyl selected from the group consisting of cyclohexyl, 4-methylcyclohexyl, 4-isopropylcyclohexyl, and mixtures thereof;

d) a heterocyclic alkyl selected from the group consisting of 2-furyl, 3-furyl, 2-thienyl, 3-thienyl, 2-pyrrolindinyl, 3-pyrrolidinyl, 2-piperazinyl, N-piperidinyl, 2-piperidinyl, 3-piperidinyl, 4-piperidinyl, N-morpholinyl, and mixtures thereof;

e) an amino unit selected from the group consisting of methylamino, dimethylamino, ethylamino, diethylamino, dicyclopropyl, and mixtures thereof;

f) a heterocyclic selected from the group consisting of amidine, 2-pyridinyl, pyrimidinyl, imidazolyl, and mixtures thereof;

g) a unit having the formula:

wherein $R^8$ is —O— and $R^9$ is selected from the group consisting of methyl, ethyl, propyl, isopropyl, n-butyl, isobutyl, and mixtures thereof; and h) mixtures thereof.

4. A composition according to claim 3 wherein R is hydrogen, methyl, and mixtures thereof.

5. A composition according to claim 1 wherein L has the formula:

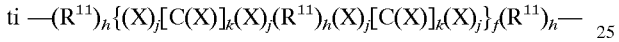

wherein $R^{11}$ is $C_1$–$C_{12}$ substituted or unsubstituted alkylene; $C_2$–$C_{12}$ substituted or unsubstituted alkenylene; substituted or unsubstituted $C_3$–$C_{12}$ cycloalkylene; substituted or unsubstituted aromatic; substituted or unsubstituted heterocyclic; X is oxygen, sulfur, $NR^{10}$ wherein $R^{10}$ is hydrogen, $C_1$–$C_4$ alkyl, phenyl, or $R^{10}$ can be taken as part of a ring bonded to another moiety in the linking group, the indices h, j, and k are each independently 0 or 1, f is from 0 to 10.

6. A composition according to claim 5 wherein said linking unit L is selected from the group consisting of:

i) —$(CH_2)_p$—, wherein p is from 0 to 12;

ii) —C(O)—;

iii) —$C(X)NR^{10}$—, wherein $R^{10}$ is hydrogen, $C_1$–$C_4$ alkyl, or mixtures thereof; X is oxygen, sulfur, $NR^{10}$, and mixtures thereof;

iv) —$C(X)R^{11}C(X)$—, wherein $R^{11}$ is $C_1$–$C_{12}$ alkylene, substituted or unsubstituted phenylene, or mixtures thereof; X is oxygen, sulfur, $NR^{10}$, and mixtures thereof;

v) —$C(X)NR^{10}C(X)$—, wherein $R^{10}$ is hydrogen, $C_1$–$C_4$ alkyl, or mixtures thereof; X is oxygen, sulfur, $NR^{10}$, and mixtures thereof;

vi) —$C(X)NR^{10}R^{11}NR^{10}C(X)$—, wherein $R^{10}$ is hydrogen, $C_1$–$C_4$ alkyl, or mixtures thereof; $R^{11}$ is $C_1$–$C_{12}$ alkylene, substituted or unsubstituted phenylene, or mixtures thereof; X is oxygen, sulfur, $NR^{10}$, and mixtures thereof;

vii) —$NR^{10}C(X)$—, wherein $R^{10}$ is hydrogen, $C_1$–$C_4$ alkyl, or mixtures thereof; X is oxygen, sulfur, $NR^{10}$, and mixtures thereof;

viii) —$NR^{10}C(X)NR^{10}$—, wherein $R^{10}$ is hydrogen, $C_1$–$C_4$ alkyl, or mixtures thereof; X is oxygen, sulfur, $NR^{10}$, and mixtures thereof;

ix) —$NR^{10}C(X)R^{11}NR^{10}$—, wherein $R^{10}$ is hydrogen, $C_1$–$C_4$ alkyl, or mixtures thereof; $R^{11}$ is $C_1$–$C_{12}$ alkylene, substituted or unsubstituted phenylene, or mixtures thereof; X is oxygen, sulfur, $NR^{10}$, and mixtures thereof;

x) —$NR^{10}R^{11}C(X)NR^{10}$—, wherein $R^{10}$ is hydrogen, $C_1$–$C_4$ alkyl, or mixtures thereof; $R^{11}$ is $C_1$–$C_{12}$ alkylene, substituted or unsubstituted phenylene, or mixtures thereof; X is oxygen, sulfur, $NR^{10}$, and mixtures thereof;

xi) —$NR^{10}C(X)R^{11}C(X)O$—, wherein $R^{10}$ is hydrogen, $C_1$–$C_4$ alkyl, or mixtures thereof; $R^{11}$ is $C_1$–$C_{12}$ alkylene, substituted or unsubstituted phenylene, or mixtures thereof; X is oxygen, sulfur, $NR^{10}$, and mixtures thereof;

xii) —$OC(X)R^{11}C(X)NR^{10}$—, wherein $R^{10}$ is hydrogen, $C_1$–$C_4$ alkyl, or mixtures thereof; $R^{11}$ is $C_1$–$C_{12}$ alkylene, substituted or unsubstituted phenylene, or mixtures thereof; X is oxygen, sulfur, $NR^{10}$, and mixtures thereof;

xiii) —$NR^{10}C(X)NR^{10}R^{11}$—, wherein $R^{10}$ is hydrogen, $C_1$–$C_4$ alkyl, or mixtures thereof; $R^{11}$ is $C_1$–$C_{12}$ alkylene, substituted or unsubstituted phenylene, or mixtures thereof; X is oxygen, sulfur, $NR^{10}$, and mixtures thereof;

xiv) —$R^{11}NR^{10}C(X)NR^{10}$—, wherein $R^{10}$ is hydrogen, $C_1$–$C_4$ alkyl, or mixtures thereof; $R^{11}$ is $C_1$–$C_{12}$ alkylene, substituted or unsubstituted phenylene, or mixtures thereof; X is oxygen, sulfur, $NR^{10}$, and mixtures thereof;

xv) —$R^{11}NR^{10}C(X)NR^{10R11}$—, wherein $R^{11}$ is hydrogen, $C_1$–$C_4$ alkyl, or mixtures thereof; $R^{R11}$ is $C_1$–$C_{12}$ alkylene, substituted or unsubstituted phenylene, or mixtures thereof; X is oxygen, sulfur, $NR^{10}$, and mixtures thereof;

xvi) —$NR^{10}$—, wherein $R^{10}$ is hydrogen, $C_1$–$C_4$ alkyl, or mixtures thereof;

xvii) —O—;

xviii) —$(R^{11})_tC(X)(R^{11})_t$—; wherein $R^{11}$ is $C_1$–$C_{12}$ alkylene, substituted or unsubstituted phenylene, or mixtures thereof; t is 0 or 1; wherein X is oxygen, sulfur, $NR^{10}$, and mixtures thereof;

xix) —$(R^{11})_tOC(O)(R^{11})_t$—; wherein $R^{11}$ is $C_1$–$C_{12}$ alkylene, substituted or unsubstituted phenylene, or mixtures thereof; t is 0 or 1;

xx) —$R^{11})_tC(O)O(R^{11})_t$—; wherein $R^{11}$ is $C_1$–$C_{12}$ alkylene, substituted or unsubstituted phenylene, or mixtures thereof; t is 0 or 1;

xxi) —$(R^{11})_tOC(O)O(R^{11})_t$—; wherein t is 0 or 1;

xxii) alkyleneoxyalkylene having the formula:

—$(R^{12}O)_qR^{13}$— wherein $R^{12}$ is $C_2$–$C_6$ linear or branched alkylene, substituted or unsubstituted phenylene; $R^{13}$ is —$(CH_2)_p$—, wherein p is from 0 to 12; q is 1 or 2;

xxiii) —S—;

xxiv) —$(R^{11})_tS(R^{11})_t$—; wherein $R^{11}$ is $C_1$–$C_{12}$ alkylene, substituted or unsubstituted phenylene, or mixtures thereof; t is 0 or 1;

xxv) —$(R^{11})_tS(O)(R^{11})_t$—; wherein $R^{11}$ is $C_1$–$C_{12}$ alkylene, substituted or unsubstituted phenylene, or mixtures thereof; t is 0 or 1;

xxvi) —$(R^{11})_tSO_2(R^{11})_t$—; wherein $R^{11}$ is $C_1$–$C_{12}$ alkylene, substituted or unsubstituted phenylene, or mixtures thereof; t is 0 or 1;

xxvii) or mixtures thereof.

7. A composition according to claim 6 wherein L is:

i) —C(O)—;

ii) —C(O)NH—;

iii) —$C(O)R^{11}C(O)$—, wherein $R^{11}$ is methylene, ethylene, propylene, butylene, or mixtures thereof;

iv) —C(O)NHC(O)—;
v) —C(O)NHR$^{11}$NHC(O)— wherein R$^{11}$ is methylene, ethylene, propylene, butylene, or mixtures thereof;
vi) —NHC(O)—;
vii) —NHC(O)NH—;
viii) —C(O)$^{11}$NH—, R$^{11}$ is C$_1$–C$_{12}$ alkylene, substituted or unsubstituted phenylene, or mixtures thereof;
ix) —NHR$^{11}$C(O)—, R$^{11}$ is C$_1$–C$_{12}$ alkylene, substituted or unsubstituted phenylene, or mixtures thereof;
x) —NH—;
xi) —O—;
xii) —R$^{11}$OC(O)R$^{11}$—; wherein R$^{11}$ is methylene, ethylene, propylene, butylene, or mixtures thereof;
xiii) —R$^{11}$C(O)OR$^{11}$—; wherein R$^{11}$ is methylene, ethylene, propylene, butylene, or mixtures thereof;
xiv) or mixtures thereof.

8. A composition according to claim 1 wherein the index z is equal to 0.

9. A composition according to claim 1 wherein the index i is equal to 1.

10. A composition according to claim 4 wherein the index i is equal to 2.

11. A composition according to claim 1 wherein [Poly] units are selected from:

i) a unit having the formula:

$$R^{19}(OR^{18})_x-$$

wherein R$^{18}$ is C$_2$–C$_{12}$ linear alkylene, C$_3$–C$_{12}$ branched alkylene, phenylene, C$_7$–C$_{12}$ alkylenearylene, and mixtures thereof; R$^{19}$ is hydrogen, C$_1$–C$_{22}$ substituted or unsubstituted, linear or branched alkyl; C$_3$–C$_{22}$ substituted or unsubstituted, linear or branched cycloalkyl; C$_2$–C$_{22}$ substituted or unsubstituted, linear or branched alkenyl; C$_2$–C$_{22}$ substituted or unsubstituted, linear or branched alkynyl; C$_6$–C$_{22}$ substituted or unsubstituted aryl; and mixtures thereof;

ii) a unit having the formula:

wherein R$^2$ is hydrogen, C$_1$–C$_4$ alkyl, and mixtures thereof; x and y are each independently from 0 to 100;

iii) a polyamine unit having the formula:

$$[H_2N-R]_{j+1}[\overset{H}{\underset{|}{N}}-R]_k[\overset{B}{\underset{|}{N}}-R]_jNH_2$$

wherein R is C$_2$–C$_{12}$ linear alkylene, C$_3$–C$_{12}$ branched alkylene, and mixtures thereof; j and k are such that the molecular weight of said polyamine does not exceed about 30,000 daltons; and iv) mixtures thereof.

12. A composition according to claim 1 wherein [Poly] has the formula:

$$R^{19}(OR^{18})_x(OR^{20})_y-$$

wherein R$^{19}$ is hydrogen, methyl, or mixtures thereof; the indices x and y have values such that the molecular weight of said [Poly] unit is from about 500 daltons to about 10,000 daltons.

13. A composition according to claim 12 wherein said [Poly] has a molecular weight of from about 1000 daltons to about 8,000 daltons.

14. A composition according to claim 13 wherein said [Poly] has a molecular weight of from about 2000 daltons to about 7500 daltons.

15. A composition according to claim 14 wherein said [Poly] has a molecular weight of from about 3000 daltons to about 7500 daltons.

16. A composition according to claim 1 wherein [Poly] is a block copolymer having the formula:

$$CH_3(EO)_{x'}(PO)_{y'}(EO)_{x''}-$$

wherein the indices x'+x"+y' have the values such that said [Poly] represents a copolymer having a molecular weight greater than or equal to about 500 daltons.

17. A composition according to claim 1 wherein [Poly] is a block copolymer having the formula:

$$CH_3(PO)_{y'}(EO)_{x'}(PO)_{y''}-$$

wherein the indices x'+y'+y" have the values such that said [Poly] represents a copolymer having a molecular weight greater than or equal to about 500 daltons.

18. A composition according to claim 1 wherein [Poly] is a block copolymer having the formula:

$$-(EO)_{x'}(PO)_{y'}(EO)_{x''}-$$

wherein the indices x'+x"+y' have the values such that said [Poly] represents a copolymer having a molecular weight greater than or equal to about 500 daltons.

19. A composition according to claim 1 wherein [Poly] is a block copolymer having the formula:

$$-(PO)_{y'}(EO)_{x'}(PO)_{y''}-$$

wherein the indices x'+y'+y" have the values such that said [Poly] represents a copolymer having a molecular weight greater than or equal to about 500 daltons.

20. A composition according to claim 1 having the formula:

wherein L is O, NH, and mixtures thereof, n is from about 45 to about 160.

21. A composition according to claim 20 wherein R is hydrogen, C$_1$–C$_8$ linear unsubstituted alkyl, and mixtures thereof.

22. A composition according to claim 21 wherein R is hydrogen, methyl, and mixtures thereof.

23. A composition according to claim 1 having the formula:

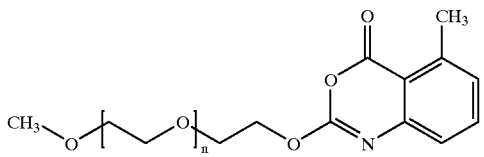

wherein n has the value such that said polymer component is derived from an MPEG having an average molecular weight of about 2000 daltons.

24. A composition according to claim 1 having the formula:

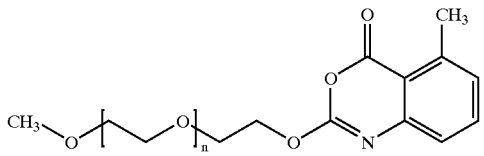

wherein n has the value such that said polymer component is derived from an MPEG having an average molecular weight of about 5000 daltons.

25. A composition according to claim 1 having the formula:

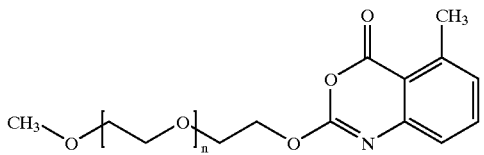

wherein n has the value such that said polymer component is derived from an MPEG having an average molecular weight of about 7000 daltons.

26. A composition according to claim 1 having the formula:

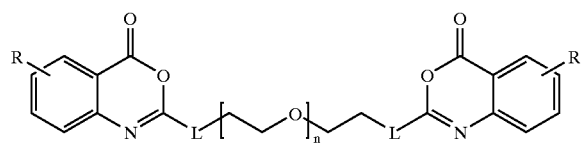

wherein L is O, NH, and mixtures thereof; n is from about 30 to about 180.

27. A composition according to claim 26 wherein R is hydrogen, $C_1$–$C_8$ linear unsubstituted alkyl, and mixtures thereof.

28. A composition according to claim 27 wherein R is hydrogen, methyl, and mixtures thereof.

29. A composition according to claim 1 having the formula:

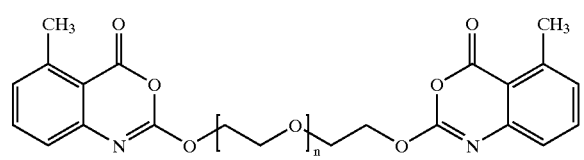

wherein n has the value such that said polymer component is derived from an PEG having an average molecular weight of about 1500 daltons.

30. A composition according to claim 1 having the formula:

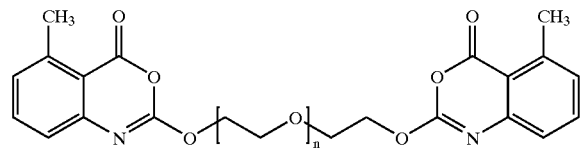

wherein n has the value such that said polymer component is derived from an PEG having an average molecular weight of about 3400 daltons.

31. A composition according to claim 1 having the formula:

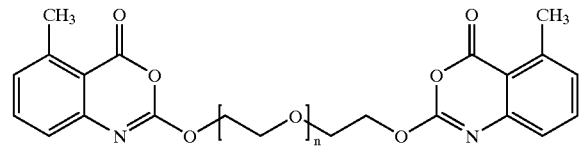

wherein n has the value such that said polymer component is derived from an PEG having an average molecular weight of about 8000 daltons.

32. A composition according to claim 1 having the formula:

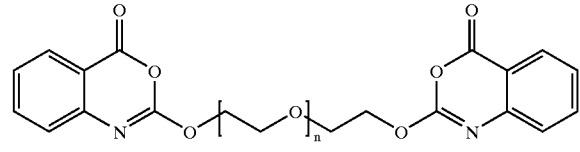

wherein n has the value such that said polymer component is derived from an PEG having an average molecular weight of about 1500 daltons.

33. A composition according to claim 1 having the formula:

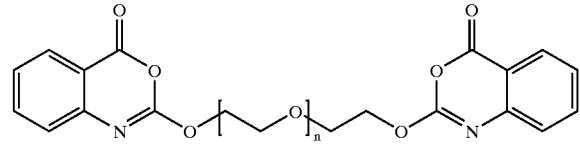

wherein n has the value such that said polymer component is derived from an PEG having an average molecular weight of about 3400 daltons.

34. A composition according to claim 1 having the formula:

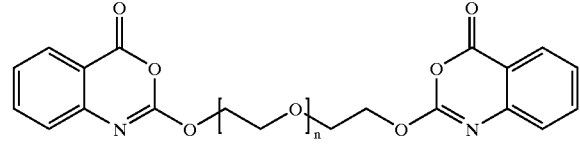

wherein n has the value such that said polymer component is derived from an PEG having an average molecular weight of about 8000 daltons.

35. A composition according to claim 1 comprising from about 0.5% to about 10% by weight, of said polymer conjugate.

36. A composition according to claim 35 comprising from about 1% to about 7.5% by weight, of said polymer conjugate.

37. A composition according to claim 36 comprising from about 1.5% to about 5% by weight, of said polymer conjugate.

38. A composition according to claim 1 further comprising from about 0.01% by weight, of an adjunct biologically active ingredient.

39. A composition according to claim 38 comprising from about 0.05% to about 5% by weight, of an adjunct biologically active ingredient.

40. A composition according to claim 39 wherein said adjunct biologically active ingredient is hexamidine.

41. A composition according to claim 1 wherein said adjunct ingredients are selected from the group consisting of petroleum-based emollients, sucrose ester fatty acids, polyethylene glycol and derivatives thereof, humectants, fatty acid esters, alkyl ethoxylates, fatty acid ester ethoxylates, fatty alcohols, polysiloxanes, propylene glycol and derivatives thereof, glycerin, glyceride, acetoglycerides, and ethoxylated glycerides of $C_{12}$–$C_{22}$ fatty acids, triethylene glycol and derivatives thereof, waxes, fatty acids, fatty alcohol ethers, propoxylated fatty alcohols, fatty esters of polyhydroxy alcohols, lanolin, kaolin, and mixtures thereof.

* * * * *

UNITED STATES PATENT AND TRADEMARK OFFICE
CERTIFICATE OF CORRECTION

PATENT NO. : 6,723,788 B1
DATED : April 20, 2004
INVENTOR(S) : Scott Edward Osborne et al.

It is certified that error appears in the above-identified patent and that said Letters Patent is hereby corrected as shown below:

Column 13,
Line 3, delete "$R^4$" and insert -- $R^{14}$ --.

Column 17,
Line 36, delete "$CCl_{13}$" and insert -- $CCl_3$ --.

Column 20,
Line 64, delete "u nit" and insert -- unit --.

Column 22,
Line 21, insert -- xvi) $-NR^{10}$-, wherein $R^{10}$ is hydrogen, $C_1$-$C_4$ alkyl, or mixtures thereof; --.

Column 36,
Line 47, delete "$C_1$-$C_{18}$" and insert -- $C_1$-$C_{12}$ --.

Column 41,
Line 26, delete "$NR^{10R11}$" and insert -- $NR^{10}R^{11}$ --.
Line 26, delete "$R^{11}$" and insert -- $R^{10}$ --.
Line 27, delete "$R^{R11}$" and insert -- $R^{11}$ --.

Column 43,
Line 6, delete "$C(O)^{11}NH$" and insert -- $C(O)R^{11}NH$ --.

Signed and Sealed this

Twenty-seventh Day of September, 2005

JON W. DUDAS
*Director of the United States Patent and Trademark Office*